United States Patent
Knepper

(10) Patent No.: US 11,234,942 B2
(45) Date of Patent: Feb. 1, 2022

(54) COMPOSITION AND METHOD FOR INHIBITING PLATELET AGGREGATION

(71) Applicant: Paul A. Knepper, Chicago, IL (US)

(72) Inventor: Paul A. Knepper, Chicago, IL (US)

( * ) Notice: Subject to any disclaimer, the term of this patent is extended or adjusted under 35 U.S.C. 154(b) by 161 days.

(21) Appl. No.: 16/275,492

(22) Filed: Feb. 14, 2019

(65) Prior Publication Data

US 2019/0175522 A1  Jun. 13, 2019

Related U.S. Application Data

(63) Continuation-in-part of application No. 15/752,458, filed as application No. PCT/US2016/047524 on Aug. 18, 2016, now abandoned.

(60) Provisional application No. 62/207,535, filed on Aug. 20, 2015.

(51) Int. Cl.
| | |
|---|---|
| *A61K 51/02* | (2006.01) |
| *A61K 31/05* | (2006.01) |
| *A61K 31/353* | (2006.01) |
| *A61P 25/28* | (2006.01) |
| *A61K 31/12* | (2006.01) |
| *A61P 7/02* | (2006.01) |
| *A61K 31/485* | (2006.01) |

(52) U.S. Cl.
CPC ............ *A61K 31/05* (2013.01); *A61K 31/12* (2013.01); *A61K 31/353* (2013.01); *A61K 31/485* (2013.01); *A61P 7/02* (2018.01); *A61P 25/28* (2018.01)

(58) Field of Classification Search
CPC ........ A61K 31/05; A61K 9/48; A61K 31/326; A61K 31/485; A61P 25/28
See application file for complete search history.

(56) References Cited

PUBLICATIONS

Gowthamarajan et al., Multiple Biological Actions of Curcumin in the Management of Diabetic Foot Ulcer Complications: A Systematic Review, Trap Med Surg Feb. 2015, 3:1. (Year: 2015).*
Cresent et al., Interactions of gallic acid, resveratrol, quercetin and aspirin at the platelet cyclooxygenase-1 level, Thromb Haemost 2009; 102: 336-346. (Year: 2009).*
Shah et al., Inhibitory Effect of Curcumin, a Food Spice from Turmeric, on Platelet-Activating Factor- and Arachidonic Acid-Mediated Platelet Aggregation through Inhibition of Thromboxane Formation and Ca2+ Signaling, Biochemical Pharmacology, vol. 58, pp. 1167-1172, 1999. (Year: 1999).*
Mazepa et al., Superactivated Platelets Thrombus Regulators, Thrombin Generators, and Potential Clinical Targets, Arterioscler Thromb Vasec Biol. 2013;33:1747-1752. (Year: 2013).*
Disanto et al., Resveratrol and quercetin down-regulate tissue factor expression by human stimulated vascular cells, Journal of Thrombosis and Haemostasis, 1: 1089-1095. (Year: 2003).*

* cited by examiner

*Primary Examiner* — Susan T Tran
(74) *Attorney, Agent, or Firm* — Olson & Cepuritis, Ltd.

(57) ABSTRACT

Pharmaceutical compositions containing a stilbene such as resveratrol, a flavonol such as quercetin, and a TLR4/MD2 receptor antagonist such as naltrexone or curcumin inhibit aggregation of superactivated platelets, block activation of the coagulation cascade, and are useful for treating microvascular diseases including neurodegenerative diseases such as Alzheimer's disease and dementia, for treating primary open-angle glaucoma, for reducing scar formation, and like afflictions that involve the coagulation cascade.

7 Claims, 22 Drawing Sheets

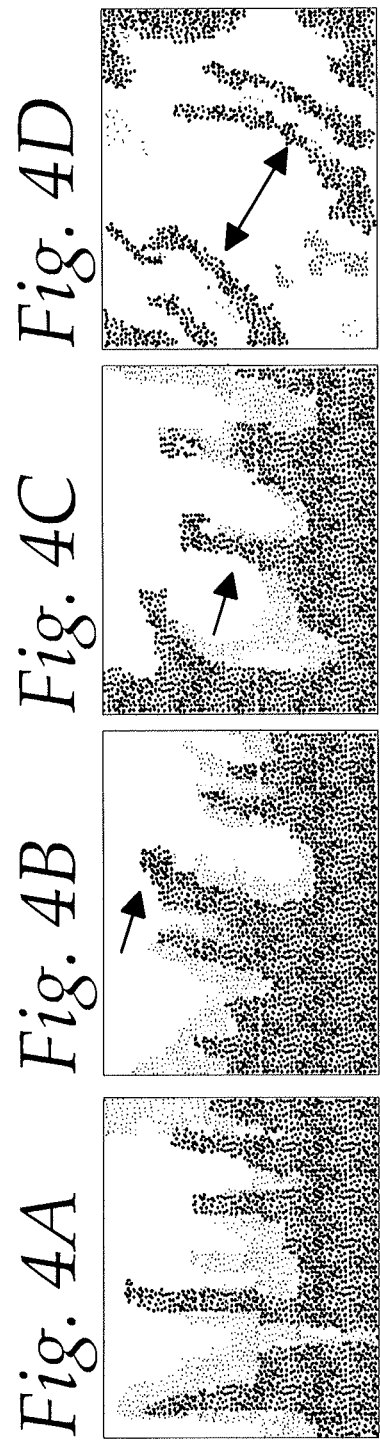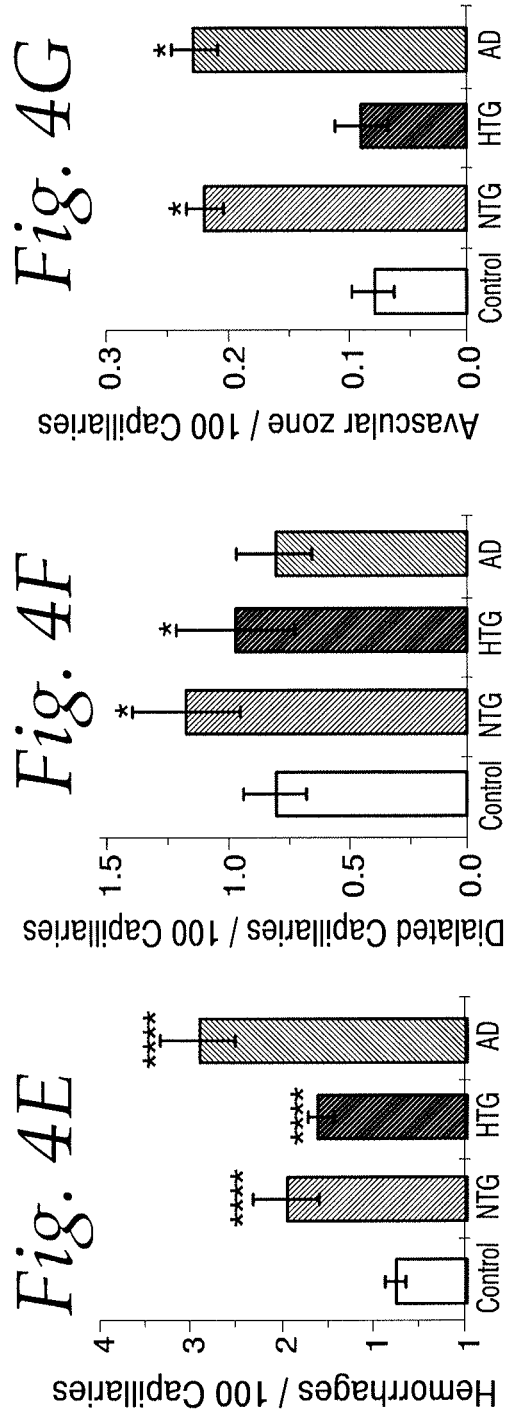

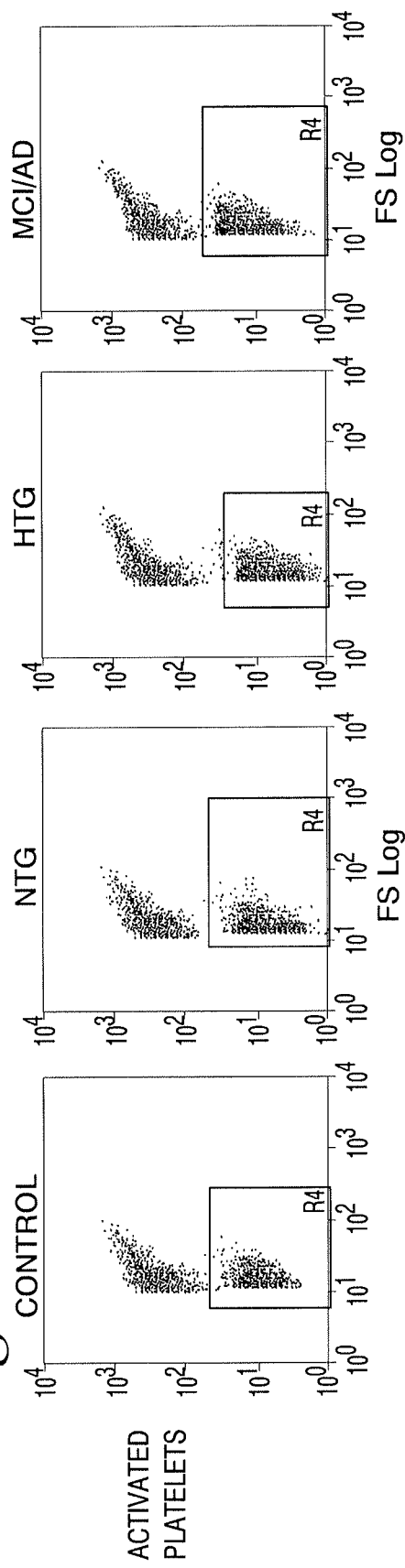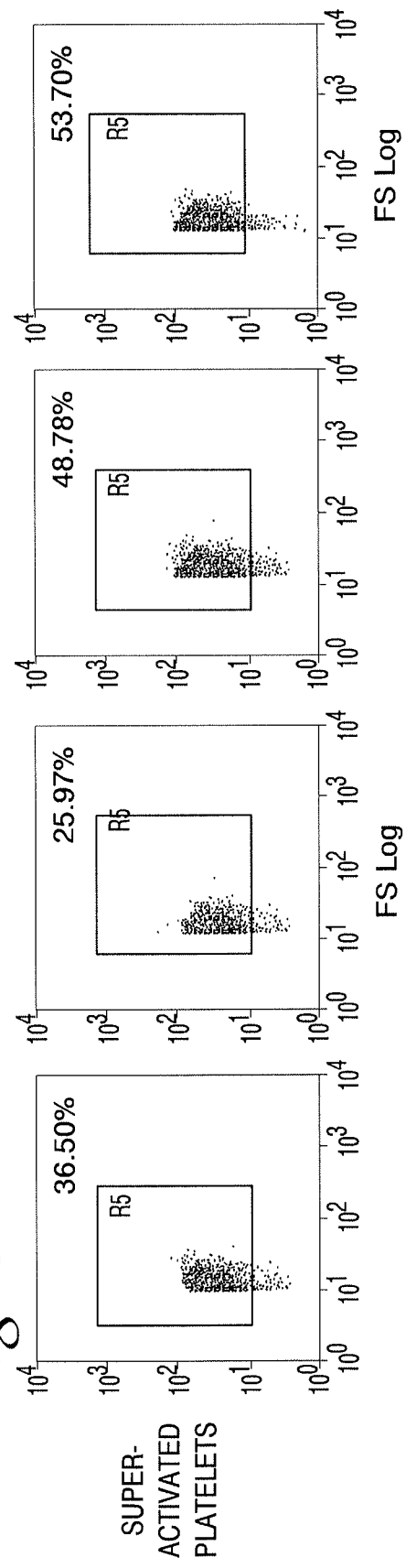

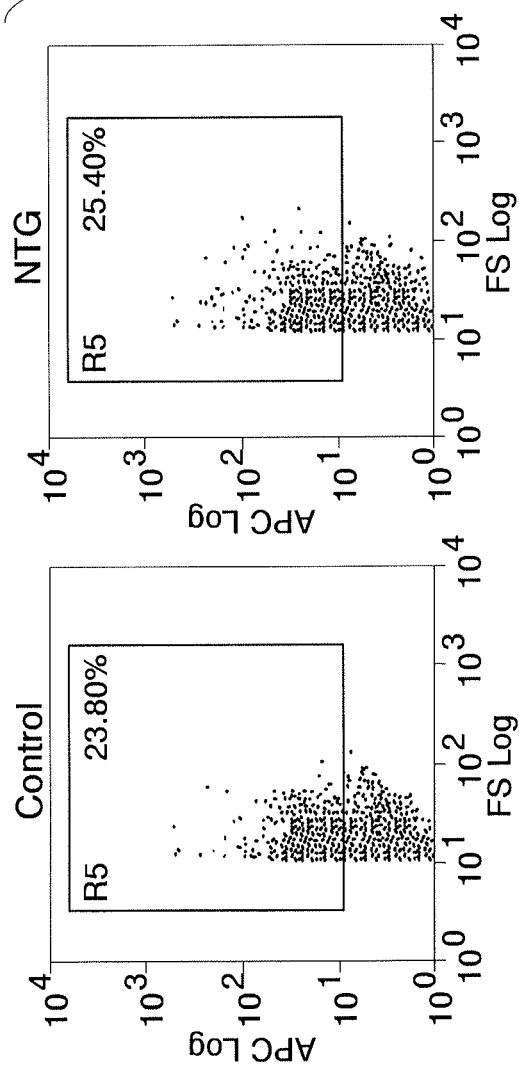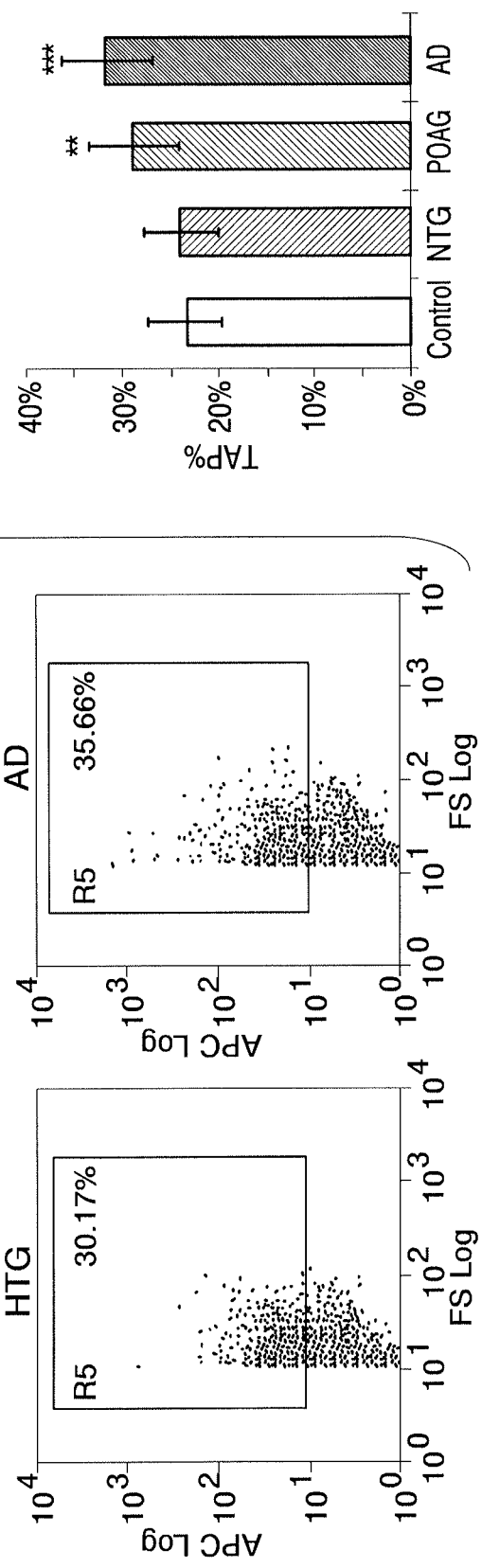

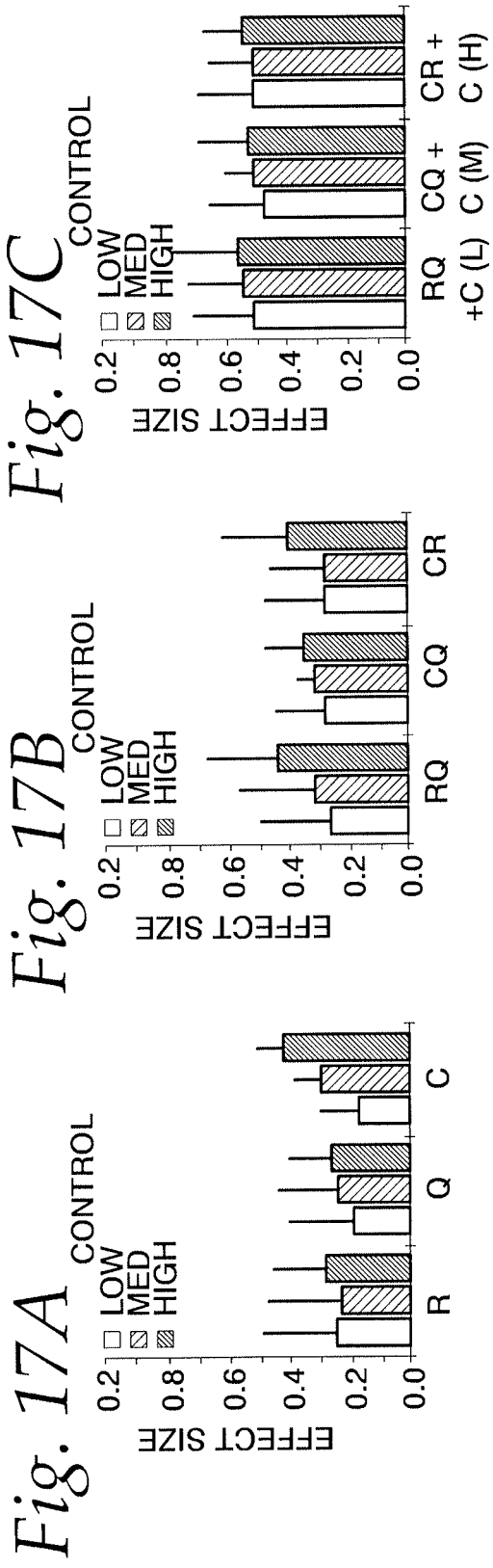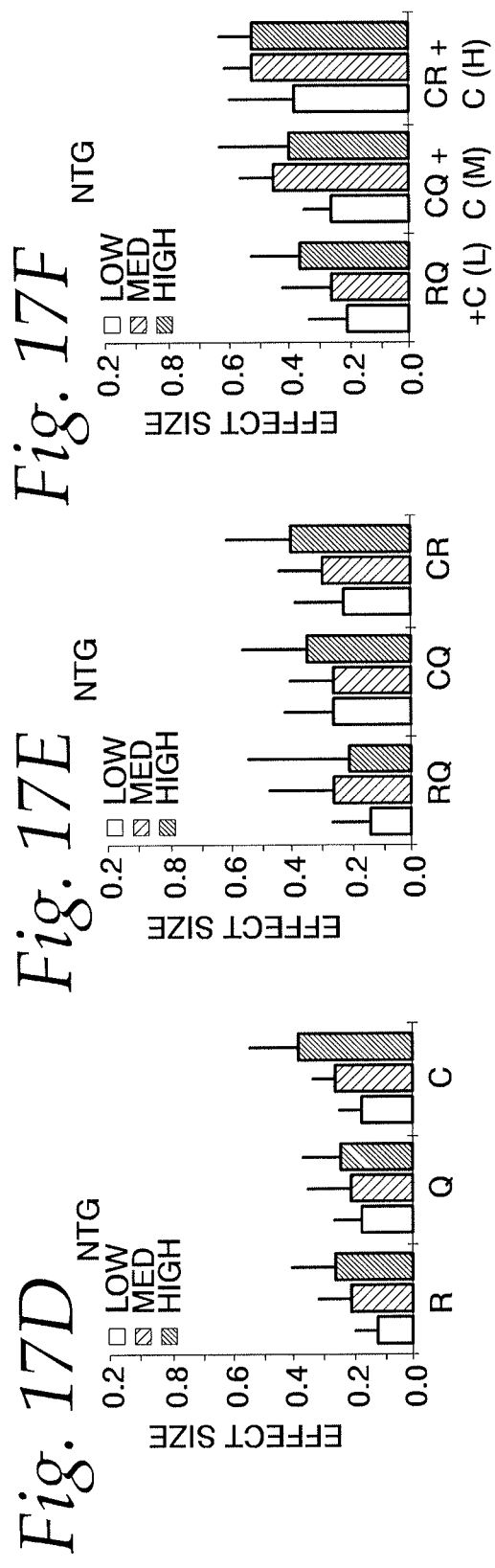

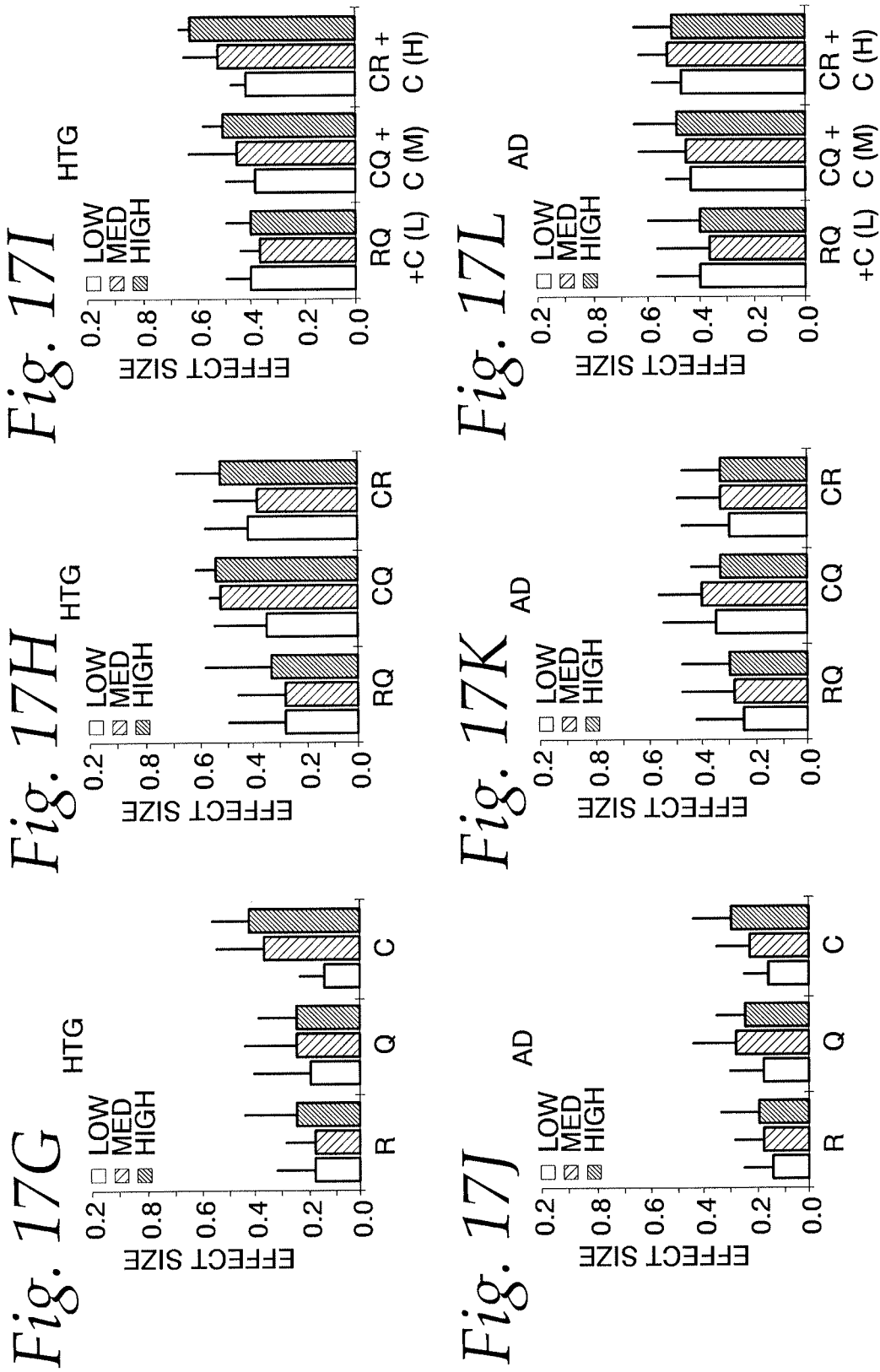

COMPOSITION AND METHOD FOR INHIBITING PLATELET AGGREGATION

CROSS-REFERENCE TO RELATED APPLICATIONS

This application is a continuation-in-part of U.S. patent application Ser. No. 15/752,458, filed on Feb. 13, 2018, which is a 371 National Stage of PCT/US2016/047524, filed on Aug. 18, 2016, and claims benefit of U.S. Provisional Application Ser. No. 62/207,535, filed on Aug. 20, 2015, each of which is incorporated herein by reference.

FIELD OF INVENTION

This invention relates to therapy involving inhibition of undesirable activation of platelets.

BACKGROUND OF THE INVENTION

Microvascular diseases account for more than one-third of human deaths worldwide. A wide number of microvascular diseases exhibit abnormal platelet functions. Platelets play an important role in arresting of bleeding, i.e., clotting. If platelets do not function as they should, obstructive clotting or serious bleeding can occur. Table 1, below, provides a sampling of conditions, and impacted populations ranging from the widespread to the less common, in which platelet function is abnormal.

TABLE 1

Prevalence and Incidence of Microvascular Diseases with Abnormal Platelet Function in the U.S. and Worldwide

|  | U.S. |  | Worldwide |  |
| --- | --- | --- | --- | --- |
| Condition | Prevalence | Incidence | Prevalence | Incidence |
| Alzheimer's disease | 5.4 million | 476,000 | 47 million |  |
| Arthritis | 52.5 million |  |  |  |
| Osteoarthritis | 30.8 million |  |  |  |
| Rheumatoid arthritis | 1.5 million |  | 94.9 million† | 2,993 million‡ |
| Cardiovascular disease | 85.6 million |  |  |  |
| Deep vein thrombosis | 600,000/year | 377,676* | 10 million |  |
| Pulmonary embolism |  |  |  |  |
| Diabetes | 29.1 million | 1.4 million | 415 million |  |
| Fibromyalgia | 10 million |  | 438 million§ |  |
| Glaucoma | 3 million |  | 60.5 million |  |
| Open-angle glaucoma | 2.7 million |  |  |  |
| POAG |  |  | 57.5 million |  |
| Heart disease | 27.6 million |  |  |  |
| Lupus | 1.5 million |  | 5 million |  |
| Myocardial infarction | 735,000/year | 635,000 |  |  |
| Scleroderma | 300,000 | 7,747** | 2.5 million |  |
| Systemic scleroderma | 75,000 | 6,456*** |  |  |
| Sjögren's Syndrome | 4 million |  |  |  |
| Stroke | 795,000 | 610,000 | 33 million |  |

*Based on an incidence rate of 117 cases per 100,000 individuals and 2016 U.S. population estimate of 322.8 million.
**Based on an incidence rate of 24 cases per 1 million individuals and 2016 U.S. population estimate of 322.8 million.
***Based on an incidence rate of 2 cases per 1 million individuals and 2016 U.S. population estimate of 322.8 million.
†Based on a prevalence of 1.3% and rounded 2016 world population estimate of 7.3 billion.
‡Based on an incidence rate of 41 cases per 100,000 individuals and 2016 world population estimate of 7.3 billion.
§Based on a prevalence of 6% and 2016 world population estimate of 7.3 billion.

Platelets (thrombocytes) are fragments of cytoplasm whose primary function is to arrest bleeding. In the blood stream, platelets travel singly, as smooth-surfaced discs. When blood vessels suffer trauma, however, platelets adhere to the exposed subendothelial fibrils, become sticky, and adhere to one another to form a hemostatic plug. The coagulation cascade is illustrated in FIG. 1.

Toll-like receptor 4 (TLR4) is a key innate immune receptor in the coagulation cascade, recognizes damage associated molecular patterns, and is important in all microvascular diseases.

A separate and discrete subpopulation of platelets exhibiting enhanced procoagulant (prothrombogenic) activity after stimulation with strong agonists has been identified. See, for example, Mazepe et al., Arterioscler Thromb Vasc Biol 33:1747-1752 (2013). This subpopulation of platelets is referred to as superactivated platelets (SAPs). SAPs are prothrombogenic platelets that are elevated in patients suffering from microvascular diseases such as primary open-angle glaucoma (POAG), a neurodegenerative disease, diabetes, etc.

Individuals afflicted with such microvascular conditions as Alzheimer's disease, glaucoma, connective tissue disorders, and autoimmune disease benefit from drugs that impact the abnormal platelet function, hemorrhaging, and/or thrombotic events associated with these conditions.

The present invention provides a composition and method for ameliorating the effects of SAPs and for treating microvascular diseases.

SUMMARY OF INVENTION

Superactivated platelet (SAP) aggregation in a patient is inhibited by administering to a subject in need of such inhibition an effective amount of a composition which comprises as active ingredients a stilbene, a flavonol, and a TLR4/MD2 receptor antagonist. A preferred stilbene is resveratrol, a preferred flavonol is quercetin, and preferred TLR4/MD2 receptor antagonists are curcumin, biologically active curcumin analogs, and naltrexone.

The stilbene, the flavonol, and the TLR4/MD2 antagonist preferably are present in the composition in a respective mol ratio in the range of about 0.1:0.1:1 to about 10:10:50.

Inhibition of superactivated platelet (SAP) aggregation is useful for treating microvascular diseases with abnormal platelet function such as primary open-angle glaucoma (POAG), Alzheimer's disease, dementia, arthritis, cardiovascular disease, deep vein thrombosis, pulmonary embolism, diabetes, fibromyalgia, heart disease, lupus, myocardial infarction, scleroderma, Sjögren's Syndrome, stroke, and the like.

Inhibition of platelet aggregation can also reduce scar formation following surgical incisions. For this purpose platelet inhibition would be applicable, including but not limited to the following: plastic surgery, ocular surgery, thoracic surgery, and the like. Also, inhibition of platelet aggregation is useful in preventing thrombus formation in blood vessels leading to deep vein thrombus, pulmonary embolism and death.

Compositions embodying this invention are useful for preventing, treating, or reversing disorders and conditions related to certain platelet abnormalities and blood diathesis in patients with microvascular diseases including Alzheimer's disease, arthritis, blood coagulation related diseases, cardiovascular disease, deep vein thrombosis, diabetes, fibromyalgia, heart disease, lupus, myocardial infarction, primary open angle glaucoma, scleroderma, stroke, thromboembolic diseases and the like.

These compositions are also useful for decreasing blood viscosity at low shear rates.

BRIEF DESCRIPTION OF DRAWINGS

In the drawings,

In FIGS. 3A-3C and 4B-4D, below, arrows identify locations of hemorrhages within the capillary bed.

FIG. 4A shows a normal nailfold capillary bed.
FIG. 4B shows a capillary hemorrhage.
FIG. 4C shows a dilated capillary ≥50 µm.
FIG. 4D shows an avascular zone ≥200 µm.
FIG. 4E shows the number of hemorrhages per 100 capillaries in normal subjects (Control), patients suffering from normal tension glaucoma (NTG), patients suffering from high tension glaucoma (HTG), and patients suffering from Alzheimer's disease (AD). In FIG. 4E, **** denotes P<0.0001.

FIG. 4F shows the number of dilated capillaries per 100 capillaries in control subjects, NTG patients, HTG patients, and AD patients. In FIG. 4F, * denotes P<0.05.

FIG. 4G shows avascular zones per 100 capillaries in control subjects, NTG patients, HTG patients, and AD patients. In FIG. 4G, * denotes P<0.05.

FIG. 5A shows flow cytometry plots of levels of activated platelets (PAC1-FITC positive indicating active integrin αIIbβ3; ungated regions) versus resting platelets and superactivated platelets (SAPs) (inactive integrin αIIbβ3; gated region R4) in control subjects, NTG patients, HTG patients and patients suffering from mild cognitive impairment (MCI) or Alzheimer's disease (AD).

FIG. 5B shows flow cytometry plots of levels of superactivated platelets (SAPs) (streptavidin-APC positive indicating both inactive integrin αIIbβ3 and surface-bound fibrinogen; gated region R5) in control subjects, NTG patients, HTG patients and MCI/AD patients.

FIG. 6C shows a flow cytometry dot plot of levels of transglutaminase-active platelets (PAC1-negative Annexin V-positive, and α2-antiplasmin positive gated regions R5) for control subjects, NTG patients, POAG patients, and AD patients.

FIG. 6D shows a flow cytometry dot plot of TAP levels for control subjects, NTG patients, POAG patients, and AD patients.  denotes P<0.01 and * denotes P<0.001.

FIG. 17A is a bar graph showing dose-response effect size of resveratrol (R), quercetin (Q), and curcumin (C) on SAP levels in vitro of control subjects.

FIG. 17B is a bar graph showing dose-response effect size of resveratrol-quercetin (RQ), curcumin-quercetin (CQ), and curcumin-resveratrol (CR) combinations on SAP levels in vitro of control subjects.

FIG. 17C is a bar graph showing dose-response effect size of resveratrol-quercetin combinations (RQ) together with low (L), medium (M), and high (H) doses of curcumin (C) on SAP levels in vitro of control subjects.

FIG. 17D is a bar graph showing dose-response effect size of resveratrol (R), quercetin (Q) and curcumin (C) on SAP levels in vitro of normal tension glaucoma (NTG) patients.

FIG. 17E is a bar graph showing dose-response effect size of resveratrol-quercetin (RQ), curcumin-quercetin (CQ), and curcumin-resveratrol (CR) combinations on SAP levels in vitro of normal tension glaucoma (NTG) patients.

FIG. 17F is a bar graph showing dose-response effect size of resveratrol-quercetin combinations (RQ) together with low (L), medium (M), and high (H) doses of curcumin (C) on SAP levels in vitro of normal tension glaucoma (NTG) patients.

FIG. 17G is a bar graph showing dose-response effect size of resveratrol (R), quercetin (Q) and curcumin (C) on SAP levels in vitro of high tension glaucoma (HTG) patients.

FIG. 17H is a bar graph showing dose-response effect size of resveratrol-quercetin (RQ), curcumin-quercetin (CQ), and curcumin-resveratrol (CR) combinations on SAP levels in vitro of high tension glaucoma (HTG) patients.

FIG. 17I is a bar graph showing dose-response effect size of resveratrol-quercetin combinations (RQ) together with low (L), medium (M), and high (H) doses of curcumin (C) on SAP levels in vitro of high tension glaucoma (HTG) patients.

FIG. 17J is a bar graph showing dose-response effect size of resveratrol (R), quercetin (Q), and curcumin (C) on SAP levels in vitro of Alzheimer's disease patients.

FIG. 17K is a bar graph showing dose-response effect size of resveratrol-quercetin (RQ), curcumin-quercetin (CQ), and curcumin-resveratrol (CR) combinations on SAP levels in vitro of Alzheimer's disease patients.

FIG. 17L is a bar graph showing dose-response effect size of resveratrol-quercetin combinations (RQ) together with low (L), medium (M), and high (H) doses of curcumin on SAP levels in vitro of Alzheimer's disease patients.

DESCRIPTION OF PREFERRED EMBODIMENTS

Superactivated platelets (SAPs) are prothrombogenic and are prevalent in afflictions and diseases that have microvascular components, such as primary open-angle glaucoma (POAG) and neurodegenerative diseases such as dementia, Alzheimer's disease, transient ischemic attacks, ischemic stroke, and the like. SAPs also negatively influence recruitment of endothelial progenitor cells (EPCs) and repair of damaged blood vessel endothelium, and are responsible for increased number of nailfold hemorrhages and hemorrhages at the optic disc in patients suffering from POAG.

It has now been found that the SAP population in a subject can be reduced by a combinatorial drug intervention strategy and provide treatment for microvascular diseases such as POAG, neurodegenerative diseases, scar formation, thromboembolic diseases, and the like.

Figure 1:
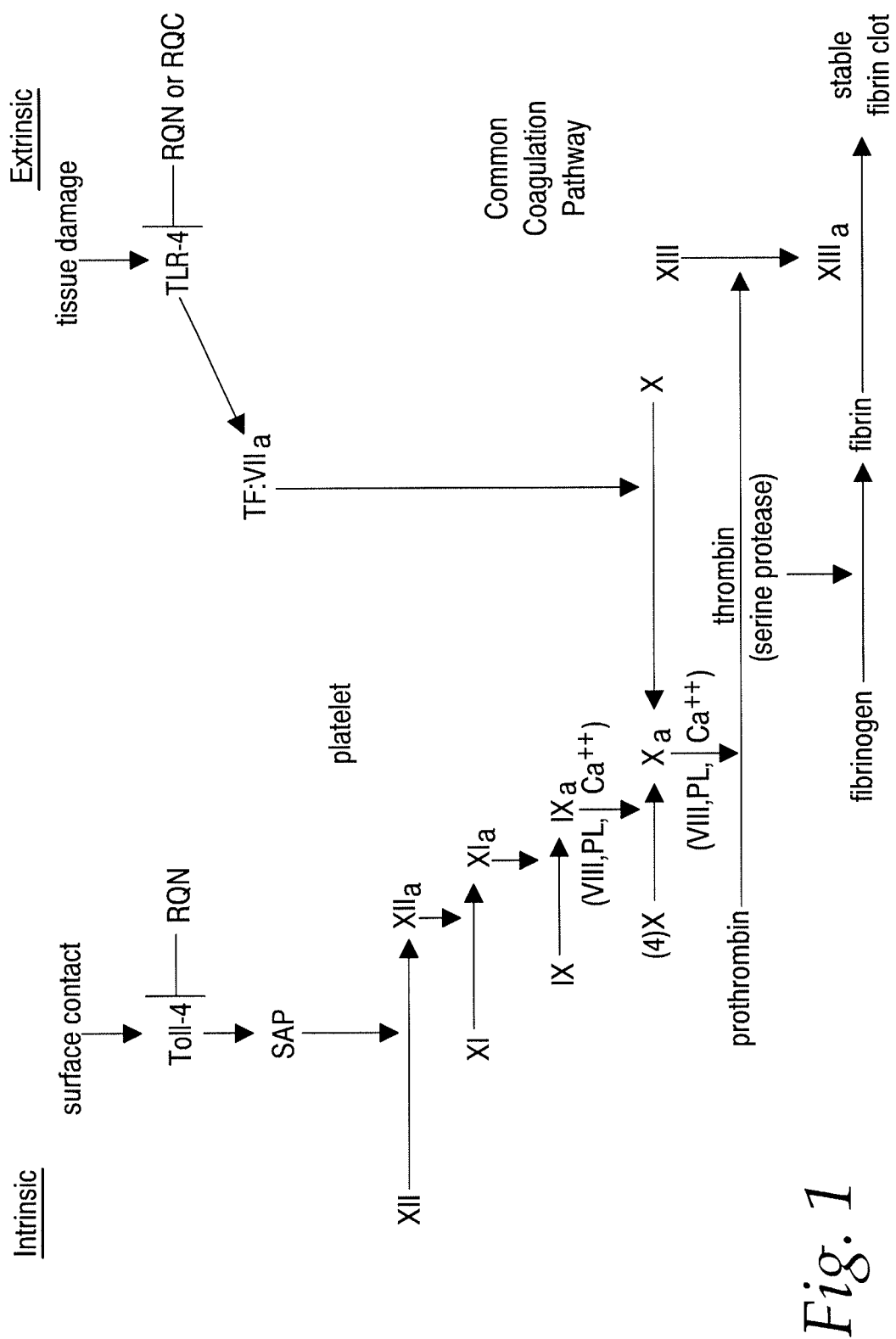
FIG. 1 is a diagram of coagulation cascade showing the intrinsic coagulation pathway (microvascular injury) and the extrinsic coagulation pathway (microvascular tissue damage). RQC denotes combinatorial drug treatment with resveratrol, quercetin and curcumin; RQN denotes combinatorial drug treatment with resveratrol, quercetin and naltrexone; TLR4 denotes toll-like receptor 4; SAP denotes superactivated platelet; XII denotes Hageman factor; XI denotes plasma thromboplastin antecedent (PTA); IX denotes plasma thromboplastin component (PTC); X denotes Stuart-Prower factor; VIII denotes antihemophilic factor (AHF); PL denotes plasma membrane phospholipid; $Ca^{++}$ denotes calcium ions; TF denotes tissue factor; VII denotes Proconvertin; and XIII denotes fibrin-stabilizing factor (FSF). For VII and X-XIII the subscript "a" indicates activated form of factor.
Figure 2:
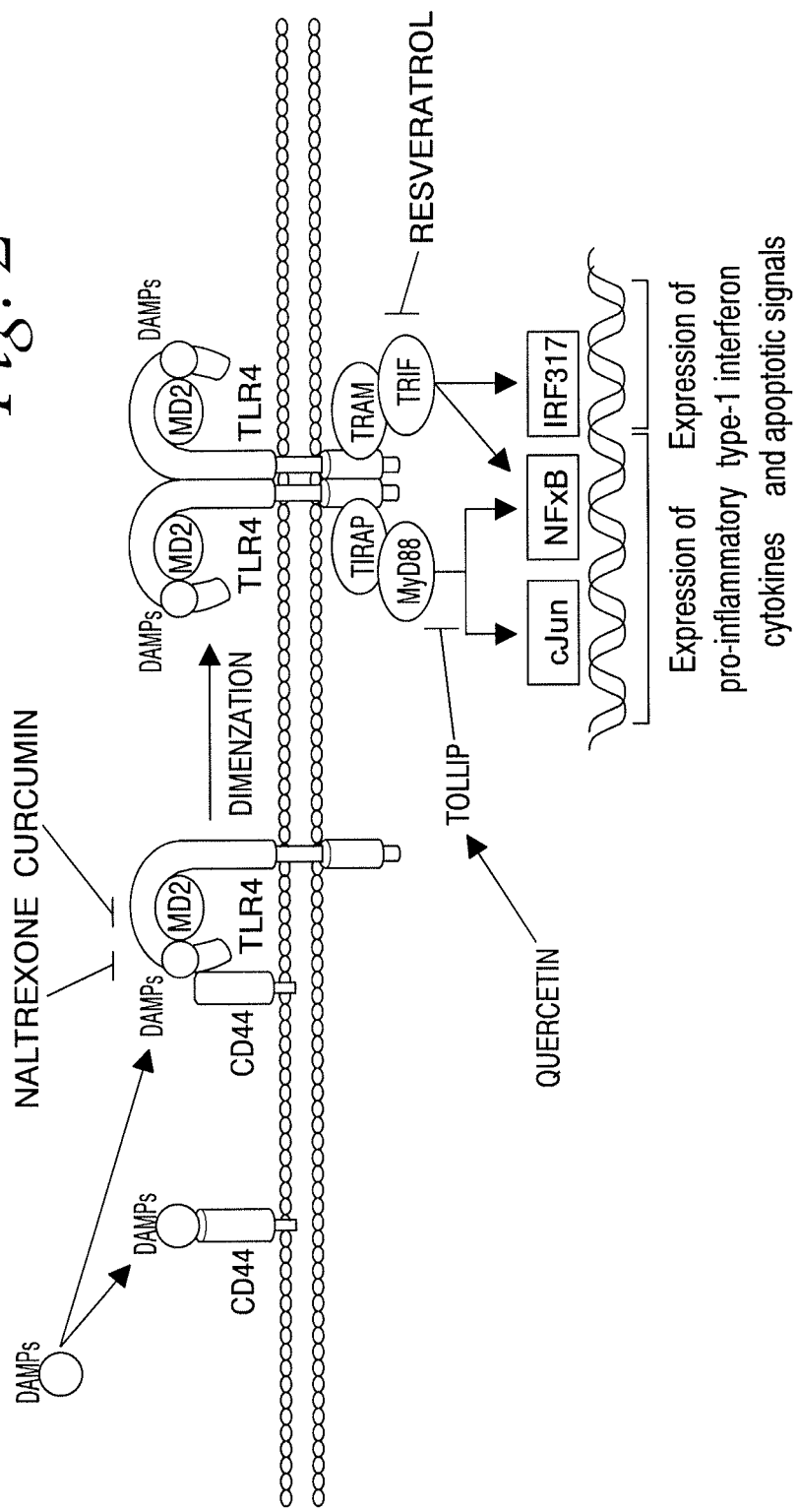
FIG. 2 is a schematic depiction of toll-like receptor 4 (TLR4) activation pathways.

The present combinatorial drug strategy has been found to inactivate the toll-like receptor 4 (TLR4), thereby blocking the first step in the coagulation cascade for the intrinsic as well as the extrinsic coagulation pathway as shown in FIGS. 1 and 2, in contradistinction to known anticoagulants such as aspirin, the nonsteroidal anti-inflammatory drugs (NSAIDs), dabigatran, and rivaroxaban. Aspirin and the NSAIDs target only platelets, dabigatran targets only thrombin, and rivaroxaban targets only Factor X.

As illustrated in FIG. 2, damage associated molecular patterns (DAMPS) bind to TLR4 along with co-accessory molecules lymphocyte antigen 96 (MD-2) and the CD 44 receptor. This results in downstream expression of pro-inflammatory cytokines and apoptotic events. Three pathways are activated: TLR4 direct pathway, MyD88 dependent pathway, and MyD88 independent pathway. TLR4 activation, in turn, leads to activation of nuclear factor kappa-β (NFkβ), toll interacting protein (TOLLIP), myeloid differentiation 88 (MyD88), TIR domain containing, adapter inducing interferon β (TRIF), TRIF-related adapter molecule (TRAM), toll interleukin one receptor adapter protein (TIRAP), interferon regulatory factor 3 (IRF-3), Jun N-terminal kinase (JNK). According to the present combinatorial drug strategy, however, a synergistic blocking of all TLR4 pathways has been achieved.

A subpopulation of prothrombogenic platelets has also been identified. This particular subpopulation exhibits transglutaminase activity when stimulated with convulxin/thrombin.

Selected embodiments of the invention are shown and described herein. These embodiments are presented by way of example only. Variations, changes and substitutions will readily occur to those skilled in the art without departing from the invention.

Unless defined otherwise, all technical and scientific terms used herein have the same meaning as is commonly understood by one skilled in the art to which this invention belongs.

As used herein and in the claims, the singular form "a," "an," and "the" includes plural references unless the context clearly dictates otherwise.

The terms "treatment," or "treating" or "ameliorating" as used in the specification and claims refer to an approach for achieving beneficial or desired results, including but not limited to a therapeutic benefit and/or a prophylactic benefit.

The term "therapeutic benefit" as used in the specification and the claims means eradication or amelioration of the underlying disorder being treated. A therapeutic benefit is achieved with the eradication or amelioration of one or more of the physiological symptoms associated with the underlying disorder such that an improvement is observed in the subject, notwithstanding that the subject may still be afflicted with the underlying disorder. For prophylactic benefit, the present compositions may be administered to a subject at risk of developing a particular affliction or disease, or to a subject reporting one or more of the physiological symptoms of a disease even though a diagnosis of the disease may not have been made.

The term "antagonist" as used in the specification and claims refers to a compound having the ability to inhibit a biological function of a target protein or receptor. Accordingly, the term "antagonist" is defined in the context of the biological role of the target protein or receptor.

The term "effective amount" or "therapeutically effective amount" refers to that amount of composition described herein that is sufficient to achieve the intended effect. The effective amount may vary depending upon the intended application on the subject and disease condition being treated, e.g., the weight and age of the subject, the severity of the disease condition, the manner of administration and the like, which can be determined readily by one skilled in the art. This term also applies to a dose that induces a particular response, e.g., reduction of platelet adhesion. The specific dose may vary depending on the particular compounds that constitute the composition, the dosing regimen to be followed, timing of administration, and the physical delivery system in which the composition is carried.

The "effective amount" or "therapeutically effective amount" may be determined by using methods known in the art such as the NFkB-Luciferase Reporter Mice Assay, the Enzyme-Linked Immunosorbent Assay (ELISA), and the like. An increase in circulating IL-6 is indicative of enhanced TLR4 expression by the platelets, thus monitoring of serum IL-6 levels can also be utilized to arrive at an effective amount of the present compositions to be administered to a particular patient.

The term "pharmaceutically acceptable excipient" as used in the specification and claims includes any and all solvents, dispersion media, coatings, antibacterial and antifungal agents, isotonic and absorption retarding agents, and the like. The use of such agents and media for pharmaceutically-active substances is well known in the art. Supplementary active ingredients can also be incorporated into the compositions described herein.

"Subject" refers to an animal, such as a mammal, for example a human. The methods described and claimed herein can be useful in both human therapeutics and veterinary applications. In some embodiments the patient is a mammal, and in some embodiments the patient is a human.

The term "unit dosage form" as used in the specification and claims refers to physically discrete units suitable as unitary dosages for human subjects and animals, each unit containing a predetermined quantity of active material calculated to produce the desired therapeutic effect in association with the required pharmaceutical diluent, carrier, or vehicle. The specifications for the novel unit dosage forms of this invention are dictated by and directly dependent on (a) the unique characteristics of the active material and the particular therapeutic effect to be achieved, and (b) the limitations inherent in the art of compounding such active material for therapeutic use in humans and animals, as disclosed in detail in the specification, these being features of the present invention. Examples of suitable unit dosage forms in accord with this invention are tablets, capsules, pills, powder packets, granules, wafers, sachets, suppositories, segregated multiples of any of the foregoing, and other forms as herein described.

The designation "µM," as used herein, denotes the micromolar concentration ($10^{-6}$ mol/L) of the indicated compound, e.g., the stilbene, the flavonol, curcumin, biologically active analogs of curcumin, naltrexone, or the like, available for contact with platelets.

Compositions containing as active ingredients a stilbene or any of its biologically active derivatives or metabolites, a flavonol or any of its biologically active derivatives or metabolites, and a TLR4/MD2 receptor antagonist or any of its biologically active derivatives or metabolites inhibit aggregation of superactivated platelets. The stilbene, the flavonol, and the TLR4/MD2 receptor antagonist preferably are present in these compositions in a respective mol ratio in the range of about 0.1:0.1:1 to about 10:10:50.

Also suitable biologically active derivatives of the foregoing are the covalently binding fluorosulfonyl ($FO_2S$—) and fluorosulfonyloxy ($FO_2SO$—) derivatives of the stilbene, the flavonol, or the TLR4/MD2 receptor antagonist. Such derivatives can be prepared as described in Dong et al., Angew. Chem. Int. Ed., 2014, vol. 53, pp. 9430-9448, and can serve by targeting active serine, tyrosine, threonine, lysine, cysteine or histidine residues.

Suitable stilbenes for the present compositions are resveratrol (3,5,4'-trihydroxy-trans-stilbene), α,β-dihydroresveratrol (3,4',5-trihydroxybibenzyl), pterostilbene (3',5'-dimethoxy resveratrol), pinosylvin (3',5-dihydroxy-trans-stilbene), piceatannol (3,5,3',4'-tetrahydroxy-trans-stilbene), and the like. Preferred stilbene is resveratrol.

Illustrative covalently binding biologically active derivatives of stilbenes are 3,5-dihydroxy-4-fluorosulfonyl-trans-stilbene, 3,5-dihydroxy-4-fluorosulfonyloxy-trans-stilbene, 3,4'-dihydroxy-5-fluorosulfonyl-trans-stilbene, 3,4'-dihydroxy-5-fluorosulfonyloxy-trans-stilbene, and the like.

Suitable flavonols are quercetin (3,3',4',5,7-pentahydroxy-2-phenylchromen-4-one), 3-hydroxyflavone, azaleatin, fisetin, galangin, gossypetin, kaempferide, kaempferol, isorhamnetin, morin, myricetin, natsudaidain, pachypodol, zhamnazin, zhamnetin, and the like. Preferred flavonol is quercetin.

Illustrative covalently binding biologically active derivatives of flavonols are 3,4',5,7-tetrahydroxy-3'-fluorosulfonyl-2-phenylchromen-4-one, 3,4',5,7-tetrahydroxy-3'-fluorosulfonyloxy-2-phenylchromen-4-one, and the like.

Suitable TLR4/MD2 receptor antagonists are naltrexone (17-(cyclopropylmethyl)-4,5α-epoxy-3,14-dihydroxymorphinan-6-one), naloxone, methylnaltrexone, naloxegol, alvimopan, curcumin, biologically active curcumin analogs and the like. Preferred TLR4/MD2 receptor antagonists are curcumin and naltrexone.

Suitable biologically active curcumin analogs are compounds represented by Formula I below, $$Ar^1\text{-L-}Ar^2 \qquad \text{I}$$

wherein $Ar^1$ is a phenyl group or a substituted phenyl group represented by Formula II:

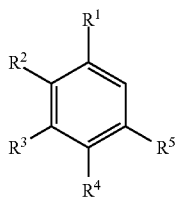

$Ar^2$ is a phenyl group represented by Formula III:

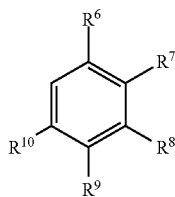

and L is a divalent linking group.

In Formulas II and III each of $R^1$ through $R^{10}$ is independently hydrogen, hydroxyl, methyl, methoxyl, dimethylamine, trifluoromethyl, chloro, fluoro, acetoxyl, cyano, or carboxymethyl.

The divalent linking group L is an alkylene or an alkenylene having 3 to 7 backbone carbon atoms wherein one or more of the backbone carbon atoms is part of a carbonyl or a secondary alcohol. The linking group can be saturated or unsaturated.

Preferably, linking group L contains at least one unsaturated carbon-carbon bond.

In a preferred embodiment, L is an alkylene or an alkenylene selected from the group consisting of: —CH=CH—CHO—, —CH=CH—(CO)—CH=CH—, —CH₂—CH₂—(CO)—CH₂—CH₂—, —CH₂—CH₂—CH(OH)—CH₂—CH₂—,

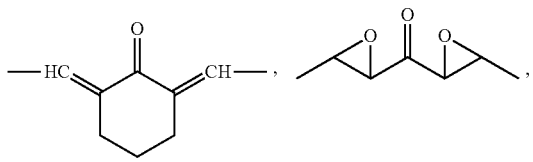

—CH=CH—(CO)—CR—C(OH)—CH=CH—,
—CH=CH—(CO)—CR₂—(CO)—CH=CH—, and
—CH=CH—(CO)—CH—C(OH)—CH=CH—; R is an alkyl or aryl group including 10 carbon atoms or less.

Illustrative covalently binding biologically active derivatives of TLR4/MD2 receptor antagonists are 17-(cyclopropylmethyl)-4,5α-epoxy-3-hydroxy-14-fluorosulfonyl-morphinan-6-one, 17-(cyclopropylmethyl)-4,5α-epoxy-3-hydroxy-14-fluorosulfonyloxy-morphinan-6-one, fluorosulfate derivatives of curcumin, and the like.

Fluorosulfate derivatives of curcumin can be produced by treating available phenolic OH groups of curcumin with sulfuryl fluoride (SO₂F₂) as described in U.S. Pat. No. 10,117,840 to Dong et al.

The compositions of the present invention can be administered topically as eye drops, ointments, and the like, as oral dosage forms such as tablets, capsules (each of which includes sustained release or timed release formulations), pills, dermal patches, nanoparticles, powders, granules, elixirs, tinctures, suspensions, syrups and emulsions. Likewise, they may also be administered in intravenous (bolus or infusion), intraperitoneal, topical (e.g., ocular eyedrop), subcutaneous, intramuscular or transdermal (e.g., patch) form, all using forms well known to those of ordinary skill in the pharmaceutical arts.

The dosage regimen utilizing the compounds of the present invention is selected in accordance with a variety of factors including type, species, age, weight, sex and medical condition of the patient; the severity of the condition to be treated and the route of administration; the renal and hepatic function of the patient; and the particular composition employed. An ordinarily skilled physician, veterinarian or clinician can readily determine and prescribe the effective amount of the drug required to prevent, counter or arrest the progress of the condition.

The amount of the aforesaid active ingredients to be administered depends on the age, weight of the patient, the particular condition to be treated, the frequency of administration, and the route of administration.

The daily dose range for the stilbene, such as resveratrol, preferably is about 2 milligrams to about 300 milligrams, for the flavonol, such as quercetin, preferably is about 1 milligram to about 150 milligrams, and for the TLR4/MD2 receptor agonist, such as naltrexone, is about 0.5 milligrams to about 300 milligrams and for curcumin about 150 milligrams to about 9500 milligrams. The daily dose can be administered as a single dose or in 3 or 4 divided doses. Veterinary dosages correspond to human dosages with the amounts administered being in proportion to the weight of the animal as compared to adult humans.

Dosage forms comprise the above-described compounds and a pharmaceutically acceptable carrier therefor. Suitable pharmaceutically acceptable carriers include solids, solutions, emulsions, dispersions, micelles, liposomes, and the like. Pharmaceutically acceptable carriers are those which render the active ingredients amenable to oral delivery, intraocular delivery, and the like.

Compositions embodying the present invention can be prepared in the form of a solid, a solution, an emulsion, a dispersion, a micelle, a liposome, and the like. The active ingredients are compounded, for example, with the usual non-toxic, pharmaceutically acceptable carriers for tablets, pellets, capsules, suppositories, solutions, emulsions, suspensions and the like. The carriers include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form.

Compositions containing the active ingredients in a form suitable for oral use are, for example, tablets, troches, lozenges, aqueous or oily suspensions, dispersible powders or granules, emulsions, hard or soft capsules, or syrups or elixirs. Compositions for oral use can be prepared according to any method known to the art for the manufacture of pharmaceutical compositions. Such formulations may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Non-toxic, pharmaceutically acceptable excipients can be, for example (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, steric acid or talc. The tablets may be uncoated or they may be coated by known techniques to delay disintegration and absorption in the gastrointestinal tract and thereby provide a sustained action over a longer period. A time delay material such as glyceryl monostearate or glyceryl distearate can be utilized as well.

In some embodiments, compositions for oral use are in the form of hard gelatin capsules wherein the active ingredient is mixed with inert solid diluent(s), for example, calcium carbonate, calcium phosphate or kaolin. In the form of soft gelatin capsules the active ingredients are mixed with water or an oil medium, for example, peanut oil, liquid paraffin, olive oil, and the like.

Example 1: Isolation and Cytometry of SAP

A venipuncture sample of 10 mL of blood is obtained from each patient. Of the 10 mL, a 3 mL aliquot of blood is added to a tube containing 0.5 mL of acid-citrate-dextrose solution (38 mM citric acid, 75 mM sodium citrate, 135 mM glucose) to prevent clotting. The aliquot is diluted with 5 mL of buffered saline glucose citrate solution (129 mM NaCl, 13.6 mM sodium citrate, 11.1 mM glucose, 1.6 mM $KH_2PO_4$, 8.6 mM $NaH_2PO_4$, pH 7.3) and centrifuged. After centrifuging at 1100 rpm for 10 minutes at room temperature, platelet rich plasma (PRP), which is the upper layer, is removed. The PRP is transferred to a new tube, leaving about 0.5 mL above the buffy coat layer. The PRP-containing tube is incubated with 10 μL of thrombin and convulxin, two agonists that activate the platelets, for five minutes. Platelets are then treated with biotinylated fibrinogen and stained with the following fluorophores: APC-streptavidin (APC-SA), FITC-PAC1, and PE-anti-CD41. PE-anti-CD41 recognizes the platelet-specific, transmembrane protein CD41. FITC-PAC1 identifies activated platelets by recognizing GP‖a‖b which increases its expression at the surface upon activation. APC-SA recognizes superactivated platelets that more readily bind the biotinylated fibrinogen to their surface.

All fluorophores are excited at 488 nm by argon laser of the flow cytometer. Their emission spectra are well separated, thereby allowing simultaneous, multi-color immunofluorescence measurements. Table 2, below, describes each fluorophore and the specific cell type it identifies.

TABLE 2

Platelet Fluorochromes

|   |   | Protein profile | Flurophores to detect |
|---|---|---|---|
| Platelets | Resting | $CD41^+$/SB-Fibrinogen$^-$/PAC1$^-$ | PE-CD41 |
|   | Activated | $CD41^+$/SB-Fibrinogen$^-$/PAC1$^+$ | PE-CD41/FITC-PAC1 |
|   | SAPs | $CD41^+$/SB-Fibrinogen$^+$/PAC1$^-$ | PE-CD41/APC-SA |

Each sample is analyzed by a Beckman Coulter CyAn flow cytometer (Beckman Coulter, Fullerton, Calif.). Results are analyzed by the Summit program (Beckman Coulter). Data analysis is conducted for SAPs after flow cytometry using the Summit program to determine the relative percentages of each of these groups per sample. The SAPs are expressed as a percentage of the total number of events in the sample.

Example 2: SAP Inhibition by Combinatorial Drug Treatment

Isolation and flow cytometry of SAPs was performed according to the procedure described in Example 1, above.

Aliquots of platelet rich plasma (PRP) were incubated with aqueous saline solutions of resveratrol only, quercetin only, naltrexone only, and with an admixture of resveratrol, quercetin and naltrexone (RQN) for a time period of 30 minutes at 37° C. Thereafter the obtained PRP samples were irradiated by an argon laser at 635 nm. Multi-color immunofluorescence was noted, and analyzed as described in Example 1, above. The obtained results are shown in Table 3, below. These data have been normalized relative to the Control (platelets incubated with thrombin and convulxin for five minutes).

TABLE 3

SAP Inactivation

|   | % SAPs | % Reduction in SAPs |
|---|---|---|
| Control | 100 | 0 |
| resveratrol, 10 μM | 53.4 | 46.6 |
| quercetin, 10 μM | 22.2 | 77.8 |
| naltrexone, 50 μM | 47.8 | 52.2 |
| resveratrol (10 μM), quercetin (10 μM) and naltrexone (50 μM) | 6.4 | 93.6 |

Data in Table 3, above, demonstrate a synergistic effect in SAP reduction by the combination of resveratrol, quercetin, and naltrexone.

Nailfold Capillaroscopy

Nailfold capillaroscopy has been used since the 1970s to study a variety of diseases associated with vascular dysfunction, e.g., scleroderma and rheumatoid arthritis [Redisch W, Messina E J, McEwen C. Capillaroscopic observations in rheumatic diseases. Ann Rheum Dis 1970, 29:244-253]. A number of studies have supported these initial findings and more recently, have also identified hemorrhages in the nailfolds of primary open-angle glaucoma (POAG) patients [Park H Y, Park S H, O H Y S, Park C K. Nail bed hemorrhage: a clinical marker of optic disc hemorrhage in patients with glaucoma. Arch Ophthalmol 2011, 129:1299-1304; Begg I S, Drance S M, Sweeney V P. Ischemic optic neuropathy in chronic simple glaucoma. Br J Ophthalmol 1971, 55:73-90; Knepper P A, Norkett W M, Green K A, Wanderling C, Kuprys P V, Giovingo M, Tanna A P, Pasquale L R. Microvascular disease in glaucoma. In: Knepper P A, Samples J R (eds): Glaucoma Research and Clinical Advances: 2016 to 2018. Amsterdam, Kugler, 2016].

Example 3: Inhibition of Hemorrhages in POAG Patients

Nailfold capillary video microscopy was performed on the fourth and fifth digit of the non-dominant hand of the patient using a JH-1004 capillaroscope. High tension POAG (n=173), normal tension POAG (NTG) (n=28), and age-matched controls (n=138). The skin was made transparent with cedar wood oil and magnified by 275× by the capillaroscope. Subjects were excluded based on previous medical history including connective tissue diseases (e.g., arthritis), autoimmune disorders (e.g., Sjögren's), malignancies and blood diathesis. Videos were taken of the nailfold and began at the medial side of the cuticle and ended at the lateral side. All videos underwent analysis by two masked observers for avascular areas, dilated capillaries, and hemorrhages. Examples of these microvascular events are illustrated in FIGS. 2A-C. An ANOVA was applied to each of the analyzed categories. A Dunnett's test was used when appropriate.

The observations are summarized in Table 4, below.

likely to occur in NTG patients suggesting a blood thrombotic event whereas extravascular hemorrhages were more common in POAG patients suggesting an injury to the capillary endothelium. Fifty-four percent of the new microvascular events observed in NTG patients were intravascular while only nine percent of POAG patients had intravascular events. The observations are summarized in Table 5, below.

TABLE 5

| Intravascular vs. Extravascular Occurrences in New Microvascular Events | | | | |
|---|---|---|---|---|
| | | Control | POAG | NTG |
| | Subjects (n) | 9/138 | 86/176 | 7/28 |
| Fresh* | Intravascular | 1 | 7 | 7 |
| | Extravascular | 9 | 64 | 6 |

*A fresh hemorrhage is bright red blood which occurs either inside (intravascular) or outside (extravascular) a capillary.

Example 4: Hemorrhages in Alzheimer's Disease (AD) Patients

Nailfold capillary beds were examined in patients with AD with mild cognitive impairment (MCI) as well as POAG

TABLE 4

| Comparison of Nailfold Capillaroscopy of Various Glaucoma and Glaucoma Suspect Patients | | | | | | | | | | | | | |
|---|---|---|---|---|---|---|---|---|---|---|---|---|---|
| | | Nailfold Hemorrhages | | | | Nailfold Dilated Capillaries (>50 μm) With | | | | Nailfold Avascular Zones (>200 μm) With | | | |
| Cohort | n | With Hemorrhages n | Events per 100 % | Capillaries | Significance | Dilated Capillaries n | Events per 100 % | Capillaries | Significance | Avascular Zones n | Events per 100 % | Capillaries | Significance |
| Control | 138 | 30 | 21.7 | 0.41 | N/A | 41 | 29.7 | 0.61 | N/A | 5 | 3.6 | 0.03 | N/A |
| POAG | 173 | 150 | 86.7 | 1.84 | p < 0.0005 | 83 | 48.0 | 0.95 | ns | 18 | 10.4 | 0.10 | ns |
| NTG | 28 | 23 | 82.1 | 3.71 | p < 0.0005 | 19 | 67.9 | 1.55 | ns | 12 | 41.4 | 0.49 | p < 0.0005 |

A statistical difference is seen between the normalized (per 100 capillaries) number of microvascular events between each of the groups compared to controls: POAG (p<0.0005) and NTG (p<0.0005). Notably 87% and 82% of POAG and NTG patients, respectively, displayed nailfold hemorrhages, compared to 21% of controls. Nailfold avascular zones were also more common in NTG patients compared to controls (p<0.0005): 4% of controls compared to 43% of NTG patients. No significance of dilated capillaries compared to controls was observed in any group.

The hemorrhages were analyzed for age (bright red suggesting a new event or dark brown suggesting hemosiderin), size (scaled accordingly), location (at the apex of the capillary loop or not) and patency (if blood was free flowing). A statistically significant difference in new microvascular events was observed when POAG and NTG patients were compared (p<0.001). Intravascular hemorrhages were more and controls. Subjects were recruited from five sites after Institutional Review Board approval. Inclusive criteria were 70 to 90 years of age. Exclusion criteria were connective tissue disease and blood diathesis. Video microscopy was performed on AD (n=10) with MCI subjects with a global clinical dementia rating ≥0.5, POAG (n=56) patients and controls (n=46). All controls had IOP <21 mm Hg OU and a cup-disc ratio of less than 0.6. All POAG patients had manifest visual field loss on standard automated perimetric tests. All AD with MCI patients denied a history of glaucoma. Microvascular events were documented by video microscopy using a JH-1004 capillaroscope at 280× magnification on the subject's fourth and fifth finger of the non-dominant hand and characterized by masked observers. The observations are summarized in Table 6, below.

TABLE 6

Comparison of Nailfold Capillaroscopy of Control, POAG, and AD Patients

| Cohort | n | Nailfold Hemorrhages Events per 100 Capillaries | Significance | Nailfold Dilated Capillaries (>50 μm) Events per 100 Capillaries | Significance | Nailfold Avascular Zones (>200 μm) Events per 100 Capillaries | Significance |
|---|---|---|---|---|---|---|---|
| Control | 46 | 0.42 | | 0.49 | | 0.02 | |
| POAG | 56 | 2.06 | $p < 0.001$ | 1.02 | $p = 0.1$ | 0.17 | $p = 0.3$ |
| AD | 10 | 2.41 | $p < 0.001$ | 0.73 | $p = 0.8$ | 0.38 | $p = 0.1$ |

Nailfold hemorrhages were noted in 100% of AD/MCI patients, 86% of POAG patients compared to 24% of controls. The mean number of hemorrhages per 100 capillaries in Alzheimer's disease patients was 2.41±2.3 (p<0.001 compared to control subjects), in POAG patients was 2.06±2.0 (p<0.001 compared to control subjects) and 0.42±0.8 in controls. Dilated capillaries were present in 60% of Alzheimer's disease patients, 45% of POAG patients and 35% of control subjects (p=0.2). Avascular zones were observed in 30% Alzheimer's disease, 13% POAG, and 4% controls (p=0.1).

As noted above, both AD with MCI and POAG patients had significantly more NF hemorrhages compared to control patients, indicating that microvascular abnormalities exist in these patients. Since the NF hemorrhages are transient biomarkers lasting less than 7 days, the outcomes of therapeutic interventions to prevent the NF hemorrhages or treatments geared at Alzheimer's disease can be readily determined by video microscopy. The etiology of these peripheral microvascular events indicates microvascular disease in AD and POAG patients.

TABLE 7

Determination of In Vivo Dose Ranges

| | Molar Mass | | | Dose Range | | |
|---|---|---|---|---|---|---|
| Compound | (g/mol) | Bioavailability | Half-life | 0.1 μM | 1 μM | 5 μM |
| Resveratrol | 228.25 | 0.1-0.4% | 2-5 hr | 29 mg | 290 mg | 1450 mg |
| Quercetin | 302.24 | 0.2-0.3% | 3-17 hr | 50 mg | 500 mg | 2500 mg |
| Naltrexone | 341.40 | 5-40% | 10 hr | 0.45 mg | 4.5 mg | 22.5 mg |
| Curcumin | 368.38 | 0.01-0.1% | 5-6 hr | 184 mg | 1840 mg | 9210 mg |

Note:
The theoretical plasma concentrations of various doses of RQC based on existing bioavailability data and found that a low-to-medium dose of each compound is theoretically obtainable (1-5 μM R, 1-5 μM Q and 0.1-5 μM C).

Example 5: Hemorrhages and Reduction by RQN

In order to test the efficacy of the resveratrol, quercetin and naltrexone combination (RQN) in preventing hemorrhages, video microscopy was performed on ten-week-old male C57/BL6 mice using a JH-1004 capillaroscope on the front foot nailfold beds under isoflurane anesthesia. Mice were given resveratrol (5 μM), quercetin (5 μM), and naltrexone (10 μM) by 20 μL intraperitoneal injections at 1 and 3 hours prior to a thrombin injection. Thrombin (15 units) was injected intraperitoneal using a 27-gauge needle in control (n=5). The observed results are compiled in Table 8, below.

TABLE 8

Comparison of Nailfold Hemorrhages in Control and RQN-Treated Mice

| | Hemorrhages | |
|---|---|---|
| Cohort | Hemorrhages/100 capillaries | % with Hemorrhages |
| Control | 18.2 ± 10 | 100% |
| Treated | 3.0 ± 7 (p < 0.02) | 80% |

The above data show the efficacy of RQN in ameliorating nailfold hemorrhages. The RQN admixture targets the innate immune toll-like receptor (TLR4) and minimizes hemorrhages by blocking both the intrinsic and extrinsic blood coagulation pathways. The combination of RQN is the only anti-platelet pharmaceutical composition known to act independently of cyclooxygenase pathway used by aspirin and other NSAID drugs. This in vivo example demonstrates the use of RQN in treating microvascular disease and the use of an anti-platelet pharmaceutical composition to prevent or at least minimize the occurrence of microhemorrhages.

Example 6: Synergistic Effects of Resveratrol, Quercetin, and Naltrexone

Figure 3C:
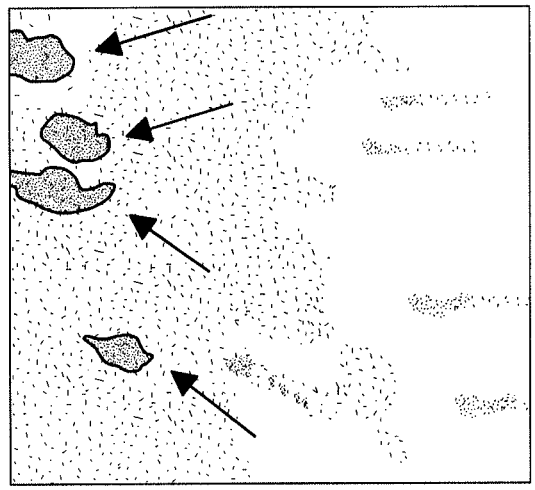
FIG. 3C is a nailfold capillaroscopy image from a 63 year old male suffering from normal tension glaucoma (NTG).
Figure 3B:
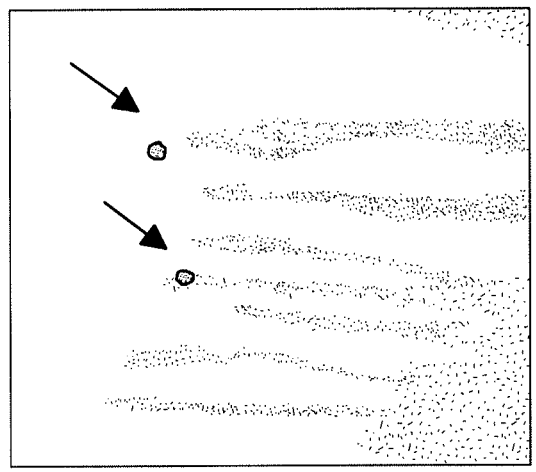
FIG. 3B is a nailfold capillaroscopy image from a 74 year old female suffering from primary open angle glaucoma (POAG).
Figure 3A:
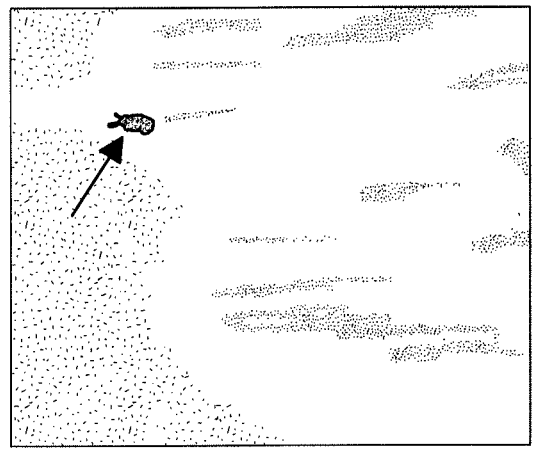
FIG. 3A is a nailfold capillaroscopy image from a 68 year old male suffering from normal tension glaucoma (NTG).

The Chou-Talalay combination index theorem was used to determine synergistic drug effects. The theorem is based on the median-effect equation to provide a common link between a single entity and multiple entities. A value <1 indicates synergism, =1 indicates additivity, and >1 indicates antagonism. Control (combination index=0.015; n=6), primary open angle glaucoma (POAG) (combination index=0.79; n=6), and Alzheimer's disease (combination index=0.48; n=6) cohorts were determined. Using 100-microliter aliquots of aqueous saline solutions it was found that at 1 μM concentration resveratrol, quercetin, and naltrexone act in a synergistic manner to reduce the amount of SAPs. This synergism allows for administration of a low dose of each of the compounds as opposed to a much higher dose of one compound. This also allows all three compounds to be administered at levels far below potentially harmful doses. The synergism of resveratrol, quercetin, and naltrexone found in control, POAG and Alzheimer's disease patients is shown in FIG. 3.

Example 7: Example of Synergism in Normal, POAG, and Alzheimer's Disease Patients Resveratrol, quercetin and naltrexone were tested in vitro using 100-microliter assay solutions with (A) a control subject platelets and (B) a POAG subject platelets. A marked reduction in SAPs at 1 μM resveratrol, 1 μM quercetin, 1 μM naltrexone in both the control subject platelets and the POAG patient's platelets was observed, representing a synergistic decrease as compared to the compounds alone. The observations are summarized in Table 9, below.

TABLE 9

Comparison of SAP Levels in Response to Varying Doses of Resveratrol, Quercetin, and Naltrexone Alone or in Combination

A)

| Control Patient 68 year old Caucasion Female Cup/disc ratio 0.3/0.3.IOP 17,17 mmHG SAP Profile | | | | | Control Patient 68 year old Caucasion Female Cup/disc ratio 0.3/0.3.IOP 17,17 mmHG SAP Profile | | | | |
|---|---|---|---|---|---|---|---|---|---|
| R (uM) | Q (uM) | N (uM) | SAP % | SAP % Change | R (uM) | Q (uM) | N (uM) | SAP % | SAP % Change |
| 0 | 0 | 0 | 36.29% | | 1 | 1 | 1 | 14.86% | −59.05% |
| 1 | 0 | 0 | 32.20% | −11.27% | 5 | 1 | 1 | 18.12% | −50.07% |
| 5 | 0 | 0 | 30.98% | −14.63% | 10 | 1 | 1 | 18.17% | −49.93% |
| 10 | 0 | 0 | 30.24% | −16.67% | 1 | 1 | 10 | 12.47% | −65.64% |
| 0 | 1 | 0 | 30.36% | −16.34% | 5 | 1 | 10 | 15.85% | −56.32% |
| 0 | 5 | 0 | 30.53% | −15.87% | 10 | 1 | 10 | 13.72% | −62.19% |
| 0 | 10 | 0 | 21.47% | −40.84% | 1 | 1 | 50 | 15.09% | −58.42% |
| 0 | 0 | 1 | 30.80% | −15.13% | 5 | 1 | 50 | 15.46% | −57.40% |
| 0 | 0 | 10 | 20.77% | −42.77% | 10 | 1 | 50 | 17.23% | −52.52% |
| 0 | 0 | 50 | 18.03% | −50.32% | 1 | 5 | 1 | 12.34% | −66.00% |
| 1 | 1 | 0 | 20.32% | −44.01% | 5 | 5 | 1 | 13.66% | −62.36% |
| 5 | 1 | 0 | 25.01% | −31.08% | 10 | 5 | 1 | 12.08% | −66.71% |
| 10 | 1 | 0 | 19.41% | −46.51% | 1 | 5 | 10 | 13.30% | −63.35% |
| 1 | 5 | 0 | 16.94% | −53.32% | 5 | 5 | 10 | 12.42% | −65.78% |
| 5 | 5 | 0 | 21.87% | −39.74% | 10 | 5 | 10 | 13.03% | −64.09% |
| 10 | 5 | 0 | 18.67% | −48.55% | 1 | 5 | 50 | 17.90% | −50.68% |
| 1 | 10 | 0 | 24.30% | −33.04% | 5 | 5 | 50 | 18.39% | −49.32% |
| 5 | 10 | 0 | 15.90% | −56.19% | 10 | 5 | 50 | 17.41% | −52.03% |
| 10 | 10 | 0 | 21.85% | −39.79% | 1 | 10 | 1 | 21.19% | −41.61% |
| 1 | 0 | 1 | 20.85% | −42.55% | 5 | 10 | 1 | 15.52% | −57.23% |
| 5 | 0 | 1 | 12.13% | −66.57% | 10 | 10 | 1 | 16.59% | −54.28% |
| 10 | 0 | 1 | 22.77% | −37.26% | 1 | 10 | 10 | 22.31% | −38.52% |
| 1 | 0 | 10 | 23.08% | −36.40% | 5 | 10 | 10 | 17.11% | −52.85% |
| 5 | 0 | 10 | 20.43% | −43.70% | 10 | 10 | 10 | 18.02% | −50.34% |
| 10 | 0 | 10 | 19.93% | −45.08% | 1 | 10 | 50 | 16.09% | −55.66% |
| 1 | 0 | 50 | 20.96% | −42.24% | 5 | 10 | 50 | 18.53% | −48.94% |
| 5 | 0 | 50 | 15.16% | −58.23% | 10 | 10 | 50 | 28.20% | −22.29% |
| 10 | 0 | 50 | 20.93% | −42.33% | | | | | |
| 0 | 1 | 1 | 17.59% | −51.53% | | | | | |
| 0 | 5 | 1 | 21.44% | −40.92% | | | | | |
| 0 | 10 | 1 | 11.67% | −67.84% | | | | | |
| 0 | 1 | 10 | 17.71% | −51.20% | | | | | |
| 0 | 5 | 10 | 15.03% | −58.58% | | | | | |
| 0 | 10 | 10 | 21.70% | −40.20% | | | | | |
| 0 | 1 | 50 | 15.65% | −56.88% | | | | | |
| 0 | 5 | 50 | 15.35% | −57.70% | | | | | |
| 0 | 10 | 50 | 12.41% | −65.80% | | | | | |

TABLE 9-continued

Comparison of SAP Levels in Response to Varying Doses of
Resveratrol, Quercetin, and Naltrexone Alone or in Combination

B)

POAG Patient
75 year old African American Female
Cup/disc ratio 0.7/0.8.IOP 27,30 mmHG
SAP Profile

| R (uM) | Q (uM) | N (uM) | SAP % | SAP % Change | R (uM) | Q (uM) | N (uM) | SAP % | SAP % Change |
|---|---|---|---|---|---|---|---|---|---|
| 0 | 0 | 0 | 56.88% |  | 1 | 1 | 1 | 23.56% | −58.58% |
| 1 | 0 | 0 | 53.30% | −6.29% | 5 | 1 | 1 | 23.31% | −59.02% |
| 5 | 0 | 0 | 53.78% | −5.45% | 10 | 1 | 1 | 23.35% | −58.95% |
| 10 | 0 | 0 | 43.53% | −23.47% | 1 | 1 | 10 | 26.13% | −54.06% |
| 0 | 1 | 0 | 49.18% | −13.54% | 5 | 1 | 10 | 26.51% | −53.39% |
| 0 | 5 | 0 | 48.25% | −15.17% | 10 | 1 | 10 | 25.86% | −54.54% |
| 0 | 10 | 0 | 43.27% | −23.93% | 1 | 1 | 50 | 40.27% | −29.20% |
| 0 | 0 | 1 | 44.27% | −22.17% | 5 | 1 | 50 | 26.22% | −53.90% |
| 0 | 0 | 10 | 40.84% | −28.20% | 10 | 1 | 50 | 35.94% | −36.81% |
| 0 | 0 | 50 | 38.93% | −31.56% | 1 | 5 | 1 | 29.27% | −48.54% |
| 1 | 1 | 0 | 47.63% | −16.26% | 5 | 5 | 1 | 27.96% | −50.84% |
| 5 | 1 | 0 | 45.72% | −19.62% | 10 | 5 | 1 | 28.34% | −50.18% |
| 10 | 1 | 0 | 43.19% | −24.07% | 1 | 5 | 10 | 41.46% | −27.11% |
| 1 | 5 | 0 | 41.54% | −26.97% | 5 | 5 | 10 | 19.60% | −65.54% |
| 5 | 5 | 0 | 50.55% | −11.13% | 10 | 5 | 10 | 28.13% | −50.55% |
| 10 | 5 | 0 | 49.62% | −12.76% | 1 | 5 | 50 | 16.67% | −70.69% |
| 1 | 10 | 0 | 44.93% | −21.01% | 5 | 5 | 50 | 32.10% | −43.57% |
| 5 | 10 | 0 | 45.51% | −19.99% | 10 | 5 | 50 | 28.58% | −49.75% |
| 10 | 10 | 0 | 46.99% | −17.39% | 1 | 10 | 1 | 34.38% | −39.56% |
| 1 | 0 | 1 | 41.69% | −26.71% | 5 | 10 | 1 | 43.45% | −23.61% |
| 5 | 0 | 1 | 46.27% | −18.65% | 10 | 10 | 1 | 22.33% | −60.74% |
| 10 | 0 | 1 | 47.04% | −17.30% | 1 | 10 | 10 | 23.54% | −58.61% |
| 1 | 0 | 10 | 42.61% | −25.09% | 5 | 10 | 10 | 19.79% | −65.21% |
| 5 | 0 | 10 | 39.50% | −30.56% | 10 | 10 | 10 | 25.32% | −55.49% |
| 10 | 0 | 10 | 44.18% | −22.33% | 1 | 10 | 50 | 29.76% | −47.68% |
| 1 | 0 | 50 | 45.53% | −19.95% | 5 | 10 | 50 | 38.17% | −32.89% |
| 5 | 0 | 50 | 50.24% | −11.67% | 10 | 10 | 50 | 44.70% | −21.41% |
| 10 | 0 | 50 | 40.90% | −28.09% |  |  |  |  |  |
| 0 | 1 | 1 | 45.02% | −20.85% |  |  |  |  |  |
| 0 | 5 | 1 | 48.00% | −15.61% |  |  |  |  |  |
| 0 | 10 | 1 | 43.87% | −22.87% |  |  |  |  |  |
| 0 | 1 | 10 | 45.35% | −20.27% |  |  |  |  |  |
| 0 | 5 | 10 | 43.06% | −24.30% |  |  |  |  |  |
| 0 | 10 | 10 | 45.52% | −19.97% |  |  |  |  |  |
| 0 | 1 | 50 | 45.24% | −20.46% |  |  |  |  |  |
| 0 | 5 | 50 | 43.02% | −24.37% |  |  |  |  |  |
| 0 | 10 | 50 | 44.87% | −21.11% |  |  |  |  |  |

In Table 9 the combination index for synergism was found to be 0.023 for the control patient and 0.08 for the POAG patient, indicating strong synergistic effects. Separate administration of the compounds was not sufficient to achieve comparable SAP decreases at low doses.

Example 8: In Vivo Trials

The in vivo effects of resveratrol, quercetin, and naltrexone (RQN) in combination was tested by an intraperitoneal (IP) injection in mice. 8-10 week old mice received a 20 μL IP injection containing 5 μM resveratrol, 5 μM quercetin, and 10 μM naltrexone. SAP levels were found to be 75% in the untreated mice, and 42% in the treated mice. Blood from the treated mice was then collected and treated again with resveratrol, quercetin, and naltrexone in low (1 μM resveratrol, 1 μM quercetin, 1 μM naltrexone), medium (5 μM resveratrol, 5 μM quercetin, 10 μM naltrexone) and high (10 μM resveratrol, 10 μM quercetin, 50 μM naltrexone) concentrations. A 43% reduction in SAPs in the mice treated with 5 μM resveratrol, 5 μM quercetin, and 10 μM naltrexone was observed compared to the untreated mice. The observed results are shown in FIG. 4 and clearly demonstrate that systemic administration of resveratrol, quercetin, and naltrexone decreases SAP percentage. Blood samples from the mice systemically treated with resveratrol, quercetin, and naltrexone were further analyzed in order to evaluate the dose response in vitro. Further treatment of SAPs in vitro showed no further SAP reduction at low and medium doses, suggesting that the receptors were sufficiently saturated during the in vivo treatment.

Example 9: Endothelial Progenitor Cells

Endothelial progenitor cells (EPCs) have been shown to play a vital role in angiogenesis and in the repair of damaged blood vessels. EPC levels are decreased in conditions that have microvascular abnormalities such as primary open-angle glaucoma (POAG) and Alzheimer's disease. Therefore, a treatment to increase the number and functionality of a patient's EPCs would reduce the symptoms of or cure the patient's condition. One method of achieving this increase in EPC counts is to perform an autologous transplant which involves collecting a blood sample from the patient, culturing the sample to enrich the EPC population, and transplanting the cells back into the patient. The transplanted EPCs allow for the repair of the damaged microvasculature. Previous studies have shown that autologous EPC transplant is an effective treatment method for advanced cardiovascular disease.

In particular, whole blood was collected from control subjects (n=4) via venipuncture, and separated via density gradient centrifugation using Lymphoprep (Stemcell Technologies, Vancouver, Canada). The peripheral blood mononuclear cell layer was then collected, resuspended in 5 ml of CFU-Hill Media (Stemcell Technologies), and plated onto a fibronectin-coated 6-well plate (Corning, Corning, N.Y.). After two days, the non-adherent cells, which are the endothelial progenitor cells (EPC), were removed and re-plated onto an 8-well chamber slide containing 5 ml of CFU-Hill Media. The cells were treated with 5 milliliters of RQN solution at low (1:1:1 µM), medium (5:5:10 µM), or high (10:10:50 µM) concentration on days 0 and 2. On the 5th day of culture, the plates were viewed for the presence of colony forming units (CFU). EPCs were identified in culture using dil-acetylated-LDL (endothelial cell marker) and FITC-ulex (fucose-residue marker) and through flow cytometry as CD34+/CD309+/CD133+ cells.

As can be seen in Table 10, below, resveratrol, quercetin, and naltrexone together increase the number of cultured EPCs.

TABLE 10

Isolation and Culture of Endothelial Progenitor Cells in the Presence of Resveratrol, Quercetin, and Naltrexone (RQN)

(A)

| Treatment | CFU Count (n = 10) |
|---|---|
| Control | 10 ± 3.16 |
| EtOH Control | 10 ± 4.39 |
| Low Concentration RQN | 11 ± 3.13 |

TABLE 10-continued

Isolation and Culture of Endothelial Progenitor Cells in the Presence of Resveratrol, Quercetin, and Naltrexone (RQN)

| | |
|---|---|
| (1 µM, 1 µM, 1 µM) | (p = 0.6) |
| Medium Concentration RQN | 12.2 ± 4.49 |
| (5 µM, 5 µM, 10 µM) | (p = 0.09) |
| High Concentration RQN | 13.1 ± 5.73 |
| (10 µM, 10 µM, 50 µM) | (p = .02) |

(B)

| Day 0 | Day 2 | Day 5 |
|---|---|---|
| 214 | 6647 | 27955 |

(A) Colony forming unit (CFU) count at Day 5 of culture. Compared to control groups, low, medium, and high concentrations of RQN gave an increase in CFU counts of 10%, 22%, and 31% respectively. (B) EPC count as determined by flow cytometry. Numbers reported as CD34+/CD309+/CD133+ cells/$10^6$ cells as determined by manual cell count (n=8).

Example 10: Safety Evaluation

Thrombin generation test, a clinical test to determine if a drug impedes blood clotting, was conducted as described below.

Resveratrol, quercetin, and naltrexone (RQN) were tested in vitro using a thrombin generation test to determine the effect of the RQN compositions on thrombin production. Low (L; 1 µM resveratrol, 1 µM quercetin, 1 µM naltrexone), medium (M; 5 µM resveratrol, 5 µM quercetin, 10 µM naltrexone), and high (H; 10 µM resveratrol, 10 µM quercetin, 50 µM naltrexone) concentrations were compared to known anti-platelet drugs. The results are shown in Table 11, below, and in FIG. 5. The RQN combination decreased thrombin in a manner similar to other commonly used anti-platelet drugs, further indicating the safety of the RQN combination.

TABLE 11

Comparison of Thrombin Reduction with Anti-Platelet Drugs

| | | Thrombin % Decrease | | |
|---|---|---|---|---|
| Drug | Concentration | Control (n = 6) | POAG (n = 6) | Alzheimer's (n = 6) |
| Resveratrol, Quercetin, Naltrexone | 1 µM resveratrol, 1 µM quercetin, 1 µM naltrexone | −101.27% | −103.38% (p = 0.9)* | −84.61% (p = 0.9) |
| Resveratrol, Quercetin, Naltrexone | 5 µM resveratrol, 5 µM quercetin, 10 µM naltrexone | −108.75% | −101.16% (p = 0.8) | −103.41% (p = 0.9) |
| Resveratrol, Quercetin, Naltrexone | 10 µM resveratrol, 10 µM quercetin, 50 µM naltrexone | −121.51% | −95.66% (p = 0.6) | −141.22% (p = 0.9) |
| Aspirin[†] | 100 µM | −76.05% | −104.39% (p = 0.4) | −75.46% (p = 0.9) |
| Ibuprofen[†] | 100 µM | −106.45% | −101.37% (p = 0.9) | −95.08% (p = 0.9) |
| Dabigatran[†] (Direct Thrombin Inhibitor) | 100 µM | −101.97% | −100.45% (p = 0.9) | −109.55% (p = 0.9) |
| Rivaroxaban[†] (Factor x Inhibitor) | 1 µM | −183.06% | −184.65% (p = 0.1) | −186.56% (p = 0.6) |

*p-values reported compared to treated controls.
[†]The anti-platelet drug doses are comparable to routine clinical doses.

Example 11: Efficacy Evaluation

The efficacy of resveratrol, quercetin, and naltrexone in preventing SAPs was evaluated.

SAPs were analyzed in the presence of resveratrol, quercetin, and naltrexone and compared to known anti-platelet drugs. Student's t-test with Turkey Post Hoc correction was used to determine significance levels comparing untreated to drug treated samples. The appropriate doses for other anti-platelet drugs were established by routine clinical use. The results are shown in Table 12, below, and FIG. 6. Co-administration of resveratrol, quercetin and naltrexone reduced the SAP levels significantly more than the known common antiplatelet drugs.

TABLE 12

Comparison of SAP Reduction with Anti-Platelet Drugs

| | | SAP % Decrease | | |
| --- | --- | --- | --- | --- |
| Drug | Concentration | Control (n = 6) | POAG (n = 6) | Alzheimer's (n = 6) |
| Resveratrol, Quercetin, Naltrexone | 1 µM resveratrol, 1 µM quercetin, 1 µM naltrexone | −63.68% ($p < 0.001$) | −66.85% ($p < 0.001$) | −29.61% ($p < 0.01$) |
| Aspirin | 100 µM | −17.00% ($p = 0.15$/ins) | −26.69% ($p < 0.1$/ins) | −17.32% ($p = 0.24$/ins) |
| Ibuprofen | 100 µM | −31.40% ($p < 0.05$) | −16.84% ($p = 0.3$/ins) | −15.30% ($p = 0.19$/ins) |
| Dabigatran (Pradaxa) (Direct Thrombin Inhibitor) | 100 µM | −0.16% ($p = 0.99$/ins) | −11.21% ($p = 0.4$/ins) | −8.09% ($p = 0.7$/ins) |
| Rivaroxaban (Xarelto) (Factor x Inhibitor) | 1 µM | −23.38% ($p < 0.1$/ins) | −48.73% ($p = 0.2$/ins) | −15.63% ($p = 0.3$/ins) |

Figure 7:
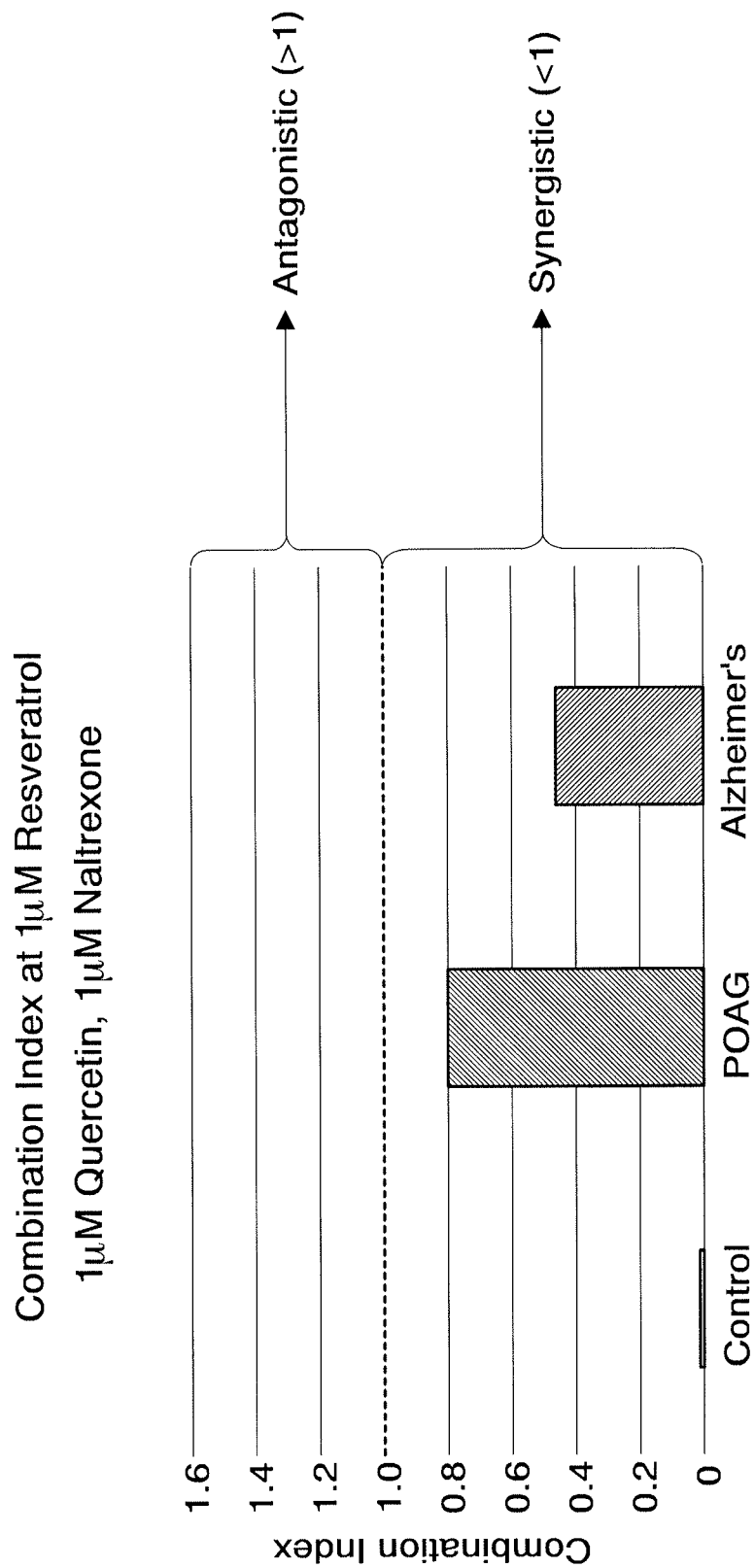
FIG. 7 is a graphical representation of the Combination Index in POAG and Alzheimer's disease patients who have received a combination of resveratrol, quercetin and naltrexone, each at 1 µM concentration.
Figure 8:
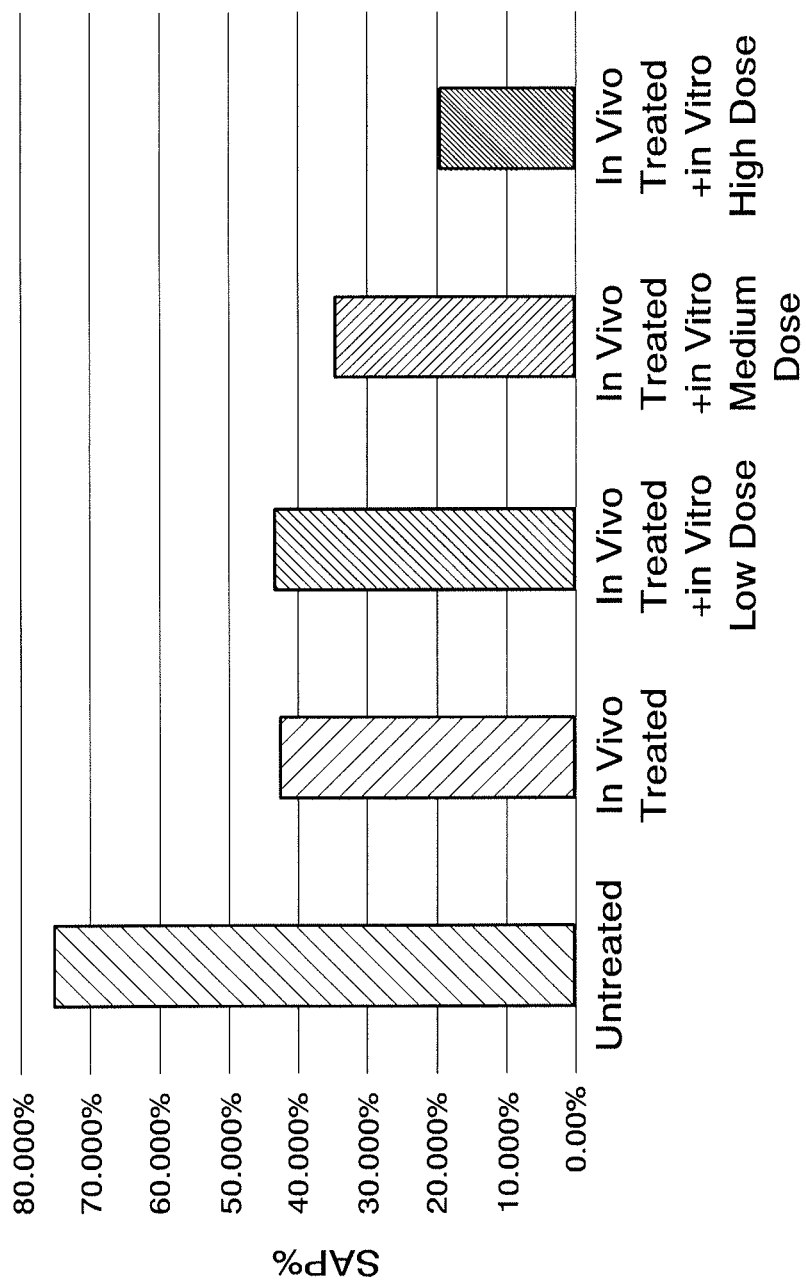
FIG. 8 is a histogram showing the effect of combined in vivo administration of resveratrol, quercetin and naltrexone to mice.
Figure 9:
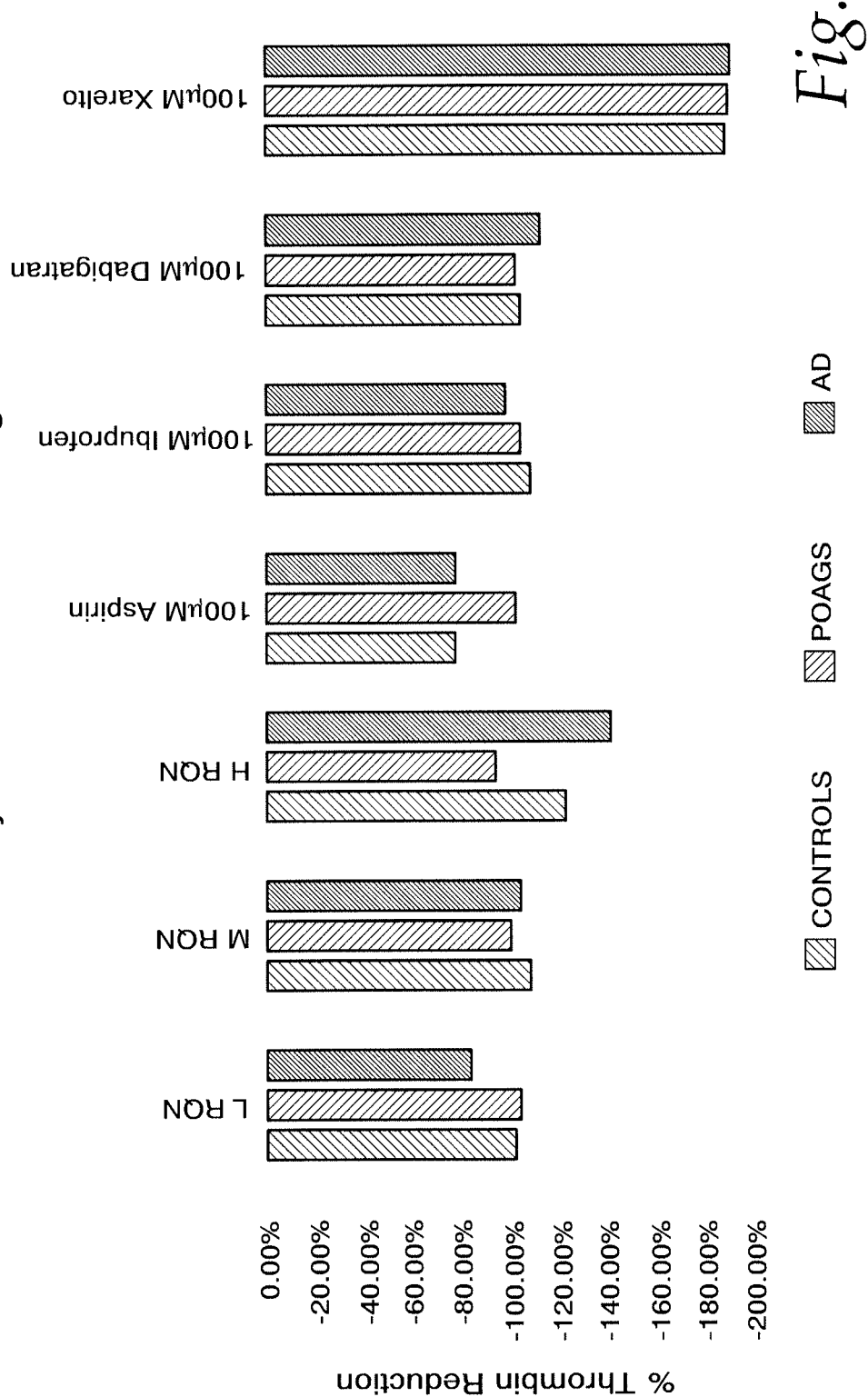
FIG. 9 is a histogram showing the results of a thrombin generation test in POAG patients and Alzheimer's disease patients.
Figure 10:
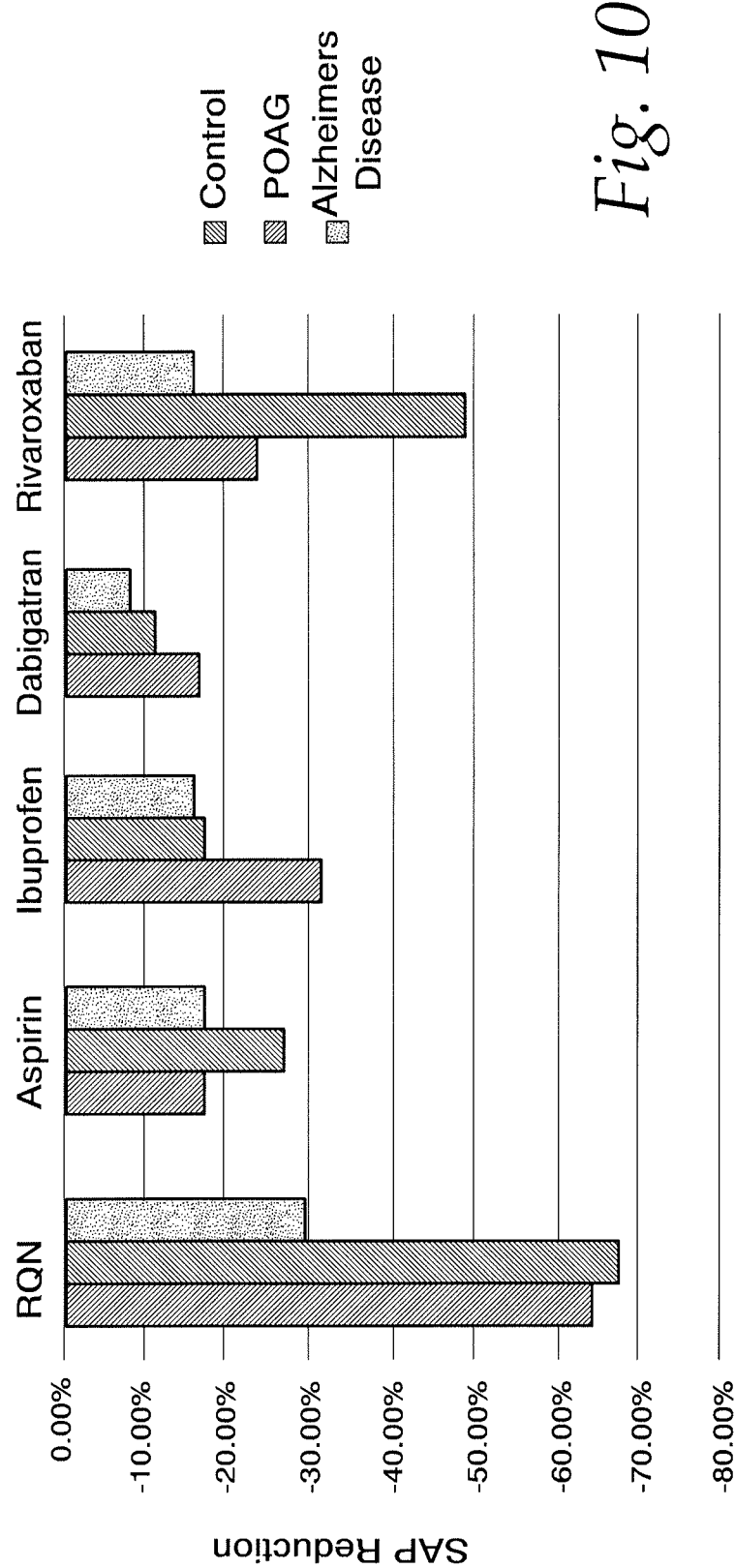
FIG. 10 is a histogram presenting the results of an evaluation of resveratrol, quercetin and naltrexone efficacy in reducing SAPs as compared to known anti-platelet drugs.
Figure 11:
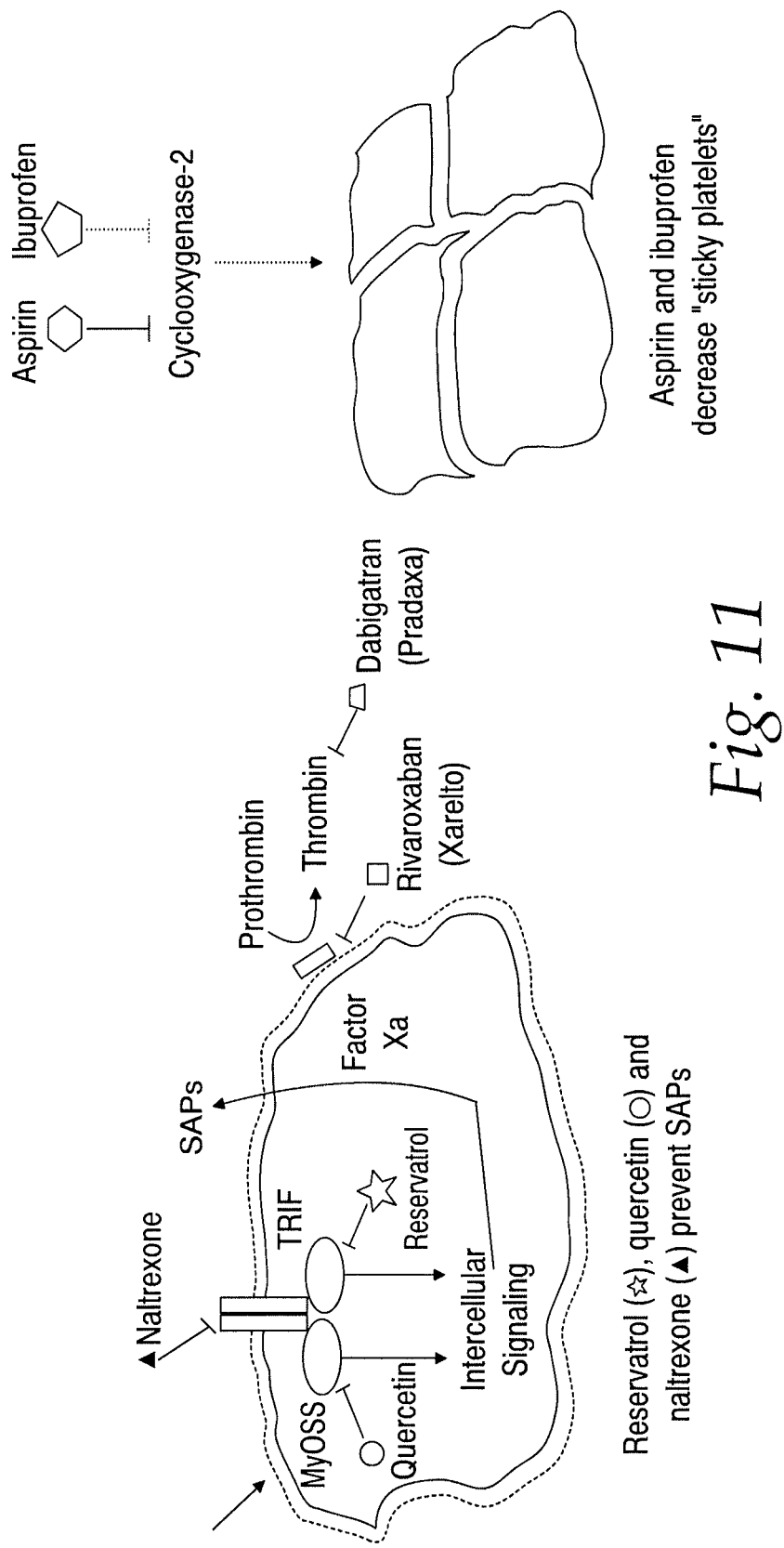
FIG. 11 is a schematic illustration of targets and signaling pathways of resveratrol, quercetin, naltrexone, and known anti-platelet drugs.

As illustrated by FIG. 7, resveratrol, quercetin, and naltrexone have a different target than existing anti-platelet drugs, and also act on a different signaling pathway.

The mechanism of resveratrol, quercetin, and naltrexone is different from that of existing anti-platelet drugs. Resveratrol, quercetin and naltrexone act together to prevent activation of an innate immune system receptor. Resveratrol, quercetin, and naltrexone together act concurrently on three legs of the TLR4 receptor—the TLR4 receptor itself, the MyD88 dependent pathway, and the MyD88 independent pathway—to inhibit subsequent intercellular signaling and superactivated platelet formation. Once a platelet is super-activated, it undergoes a phosphatidyl membrane flip, exposing negatively charged residues. This negative charge then serves as a platform for Factor Xa, which converts pro-thrombin to thrombin in the coagulation cascade. Rivaroxaban acts as a Factor Xa inhibitor, and dabigatran serves as a direct thrombin inhibitor. Aspirin and ibuprofen act on cyclooxygenase-2 to prevent "sticky platelets." The combined administration of resveratrol, quercetin, and naltrexone represents a unique breakthrough therapy for platelet associated diseases. Resveratrol, quercetin, and naltrexone co-act to suppress platelet activation, in marked contrast to existing drugs which are effective only after platelets have been activated.

This difference in mechanism has significant safety implications. Current anti-platelet medications such as aspirin increase the risk of gastrointestinal bleeding. Using aspirin in combination with clopidogrel or warfarin also increases the risk of upper gastrointestinal bleeding. Blockade of COX-1 by aspirin increases the gastric mucosal erosion. Aspirin causes an increased risk of cerebral microbleeds since they often occur prior to ischemic stroke or intracerebral hemorrhages, and Alzheimer's disease. In addition, current anti-platelet drugs can lead to uncontrolled bleeding and death. Aspirin and rivaroxaban effects on platelets are irreversible, whereas dabigatran can be reversed by praxbind. The combined anti-platelet effects of resveratrol, quercetin, and naltrexone can be reversed by an opiate analog, if necessary.

As evidenced by data in Table 12 and FIG. 6, current anti-platelet drugs do not significantly alter SAP production, except for rivaroxaban in POAG patients. However, the inhibition of the TLR4 receptor by the RQN combination, a receptor involved in the innate immune system, significantly decreases the number of SAPs.

Example 12: Systematic Capillary Abnormalities

Nailfold capillaroscopy was used to visualize and quantify systemic capillary abnormalities in the nailfold capillary bed. It was found that nailfold capillary abnormalities are increased in patients suffering from Alzheimer's disease (AD), high tension glaucoma (HTG) and normal tension glaucoma (NTG) as shown in FIGS. 4A-4G and Table 13, below.

TABLE 13

Descriptive Statistics of Nailfold Capillary Abnormalities by Cohort

| | | Hemorrhages/100 Capillaries | | | | Dilated Capillaries/100 Capillaries | | | | Avascular Zones/100 Capillaries | | | |
| --- | --- | --- | --- | --- | --- | --- | --- | --- | --- | --- | --- | --- | --- |
| | n | Mean (SD) | P-value* | P-value | P-value | Mean (SD) | P-value | P-value | P-value | Mean (SD) | P-value | P-value | P-value |
| Control | 304 | 0.78 (1.58) | ref | — | — | 0.81 (1.67) | ref | — | — | 0.08 (0.31) | ref | — | — |
| Caucasian | 194 | 0.83 (1.70) | — | — | ref | 1.03 (1.92) | — | — | ref | 0.11 (0.36) | — | — | ref |

TABLE 13-continued

Descriptive Statistics of Nailfold Capillary Abnormalities by Cohort

| | | Hemorrhages/100 Capillaries | | | | Dilated Capillaries/100 Capillaries | | | | Avascular Zones/100 Capillaries | | | |
|---|---|---|---|---|---|---|---|---|---|---|---|---|---|
| | n | Mean (SD) | P-value* | P-value | P-value | Mean (SD) | P-value | P-value | P-value | Mean (SD) | P-value | P-value | P-value |
| African American | 57 | 0.89 (1.56) | — | — | 0.58 | 0.43 (0.96) | — | — | 0.001 | 0.03 (0.21) | — | — | 0.03 |
| HTG | 272 | 1.62 (1.83) | <0.0001 | ref | — | 0.97 (1.57) | 0.03 | ref | — | 0.09 (0.27) | 0.53 | ref | — |
| Caucasian | 145 | 1.32 (1.50) | — | — | ref | 1.35 (0.15) | — | — | ref | 0.11 (0.29) | — | — | ref |
| African American | 100 | 2.24 (2.25) | — | — | <0.0001 | 0.52 (1.10) | — | — | <0.0001 | 0.07 (0.25) | — | — | 0.48 |
| NTG | 69 | 2.01 (2.78) | <0.0001 | 0.52 | ref | 1.16 (1.79) | 0.02 | 0.34 | ref | 0.02 (0.41) | 0.02 | 0.05 | ref |
| AD | 23 | 2.71 (3.38) | <0.0001 | 0.09 | 0.20 | 0.50 (0.87) | 0.79 | 0.32 | 0.19 | 0.28 (0.62) | 0.01 | 0.07 | 0.93 |

*Mann-Whitney U test.

Mean hemorrhages and dilated capillaries were significantly higher in HTG and NTG than in controls and trended upward in NTG compared with HTG (FIG. 1E; Table 13). Avascular zones were significantly increased in NTG (P=0.02) but not HTG patients compared with controls (FIG. 1G). Hemorrhages (P<0.001) and avascular zones (P=0.01) but not dilated capillaries were significantly higher in AD than in controls (FIG. 1F). In addition, capillary hemorrhages were significantly increased in African American HTG patients compared with Caucasian HTG patients; no differences were observed between Caucasian and African American control subjects.

Example 13: Superactivated Platelet Levels

Figure 5C:
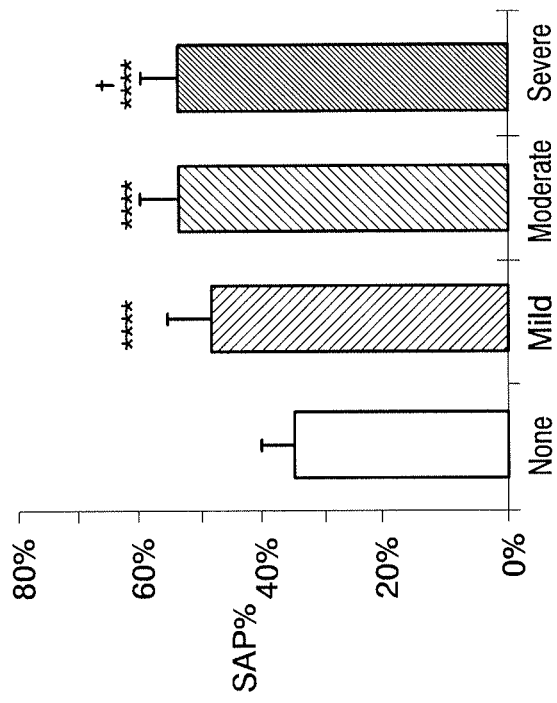
FIG. 5C shows mean superactivated platelet (SAP) levels in control subjects, NTG patients, HTG patients, and MCI/AD patients. **** denotes P<0.0001 compared with control, tttt denotes P<0.0001 compared with NTG patients.
Figure 5D:
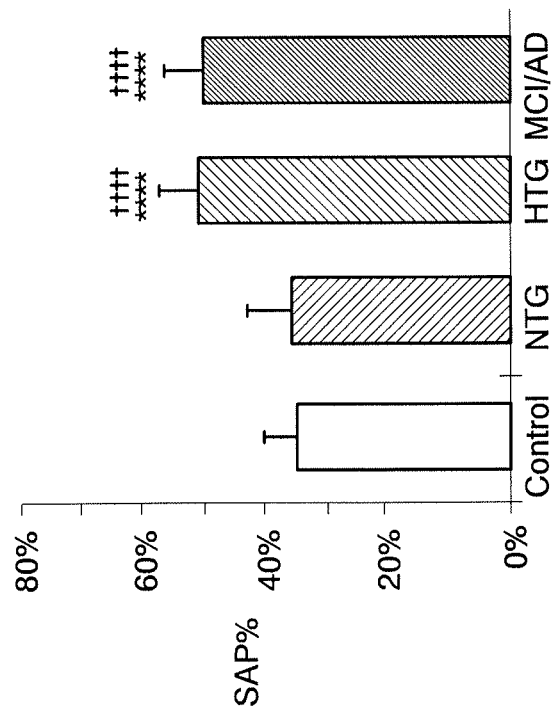
FIG. 5D shows superactivated platelet levels in HTG patients analyzed by visual field loss. **** denotes P<0.0001 compared with control, t denotes P<0.05 compared with mild visual field loss.

Flow cytometry method described by Dale et al., Nature 415 (6868):175-179 (January 2002), was used to quantitate platelet activation status, i.e., resting, activated, and superactivated (FIGS. 5A-5B). Superactivated platelets (SAPs) are a highly procoagulant and prothrombotic subtype of activated platelets. SAP levels were significantly higher in HTG patients than in healthy controls (P<0.0001) or NTG patients (P<0.0001) (FIG. 5C). Baseline SAPs, i.e., SAP levels without agonist stimulation, were significantly increased in HTG and AD but not in NTG. SAP levels were associated with HTG disease progression as defined by visual field loss. HTG patients with mild, moderate, and severe visual field loss all had significantly higher SAP levels than control subjects. Those with severe visual field loss had significantly higher SAPs than those with mild visual field loss (P<0.05) (FIG. 5E).

Example 14: Transglutaminase-Active Platelet Levels

Figure 6A:
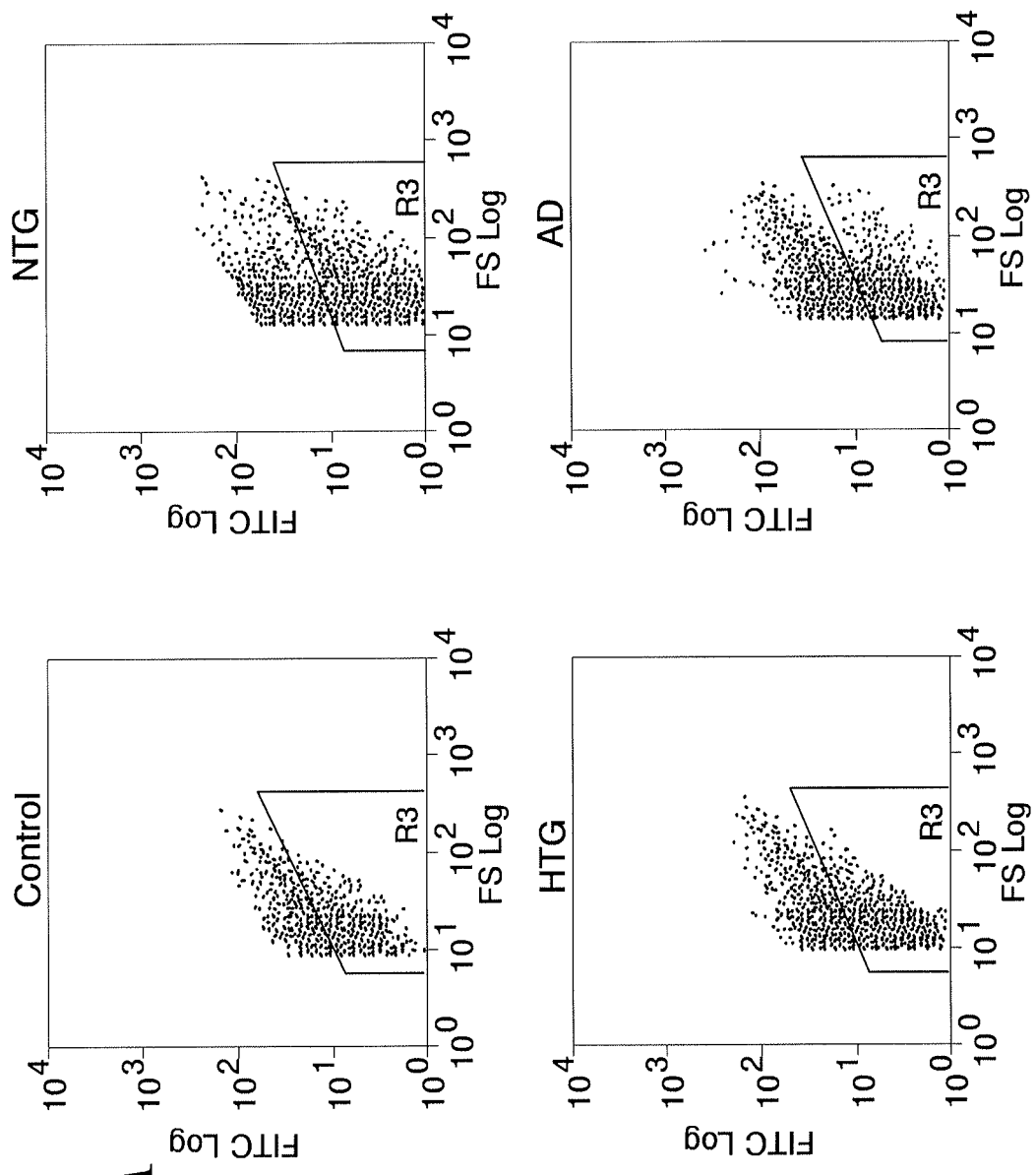
FIG. 6A shows a flow cytometry dot plot of levels of activated (active integrin αIIbβ3; PAC1-positive ungated regions) and resting platelets plus SAPs (inactive integrin αIIbβ3; PAC1-negative gated regions R3) for control subjects, NTG patients, primary open-angle glaucoma (POAG) patients and AD patients.
Figure 6B:
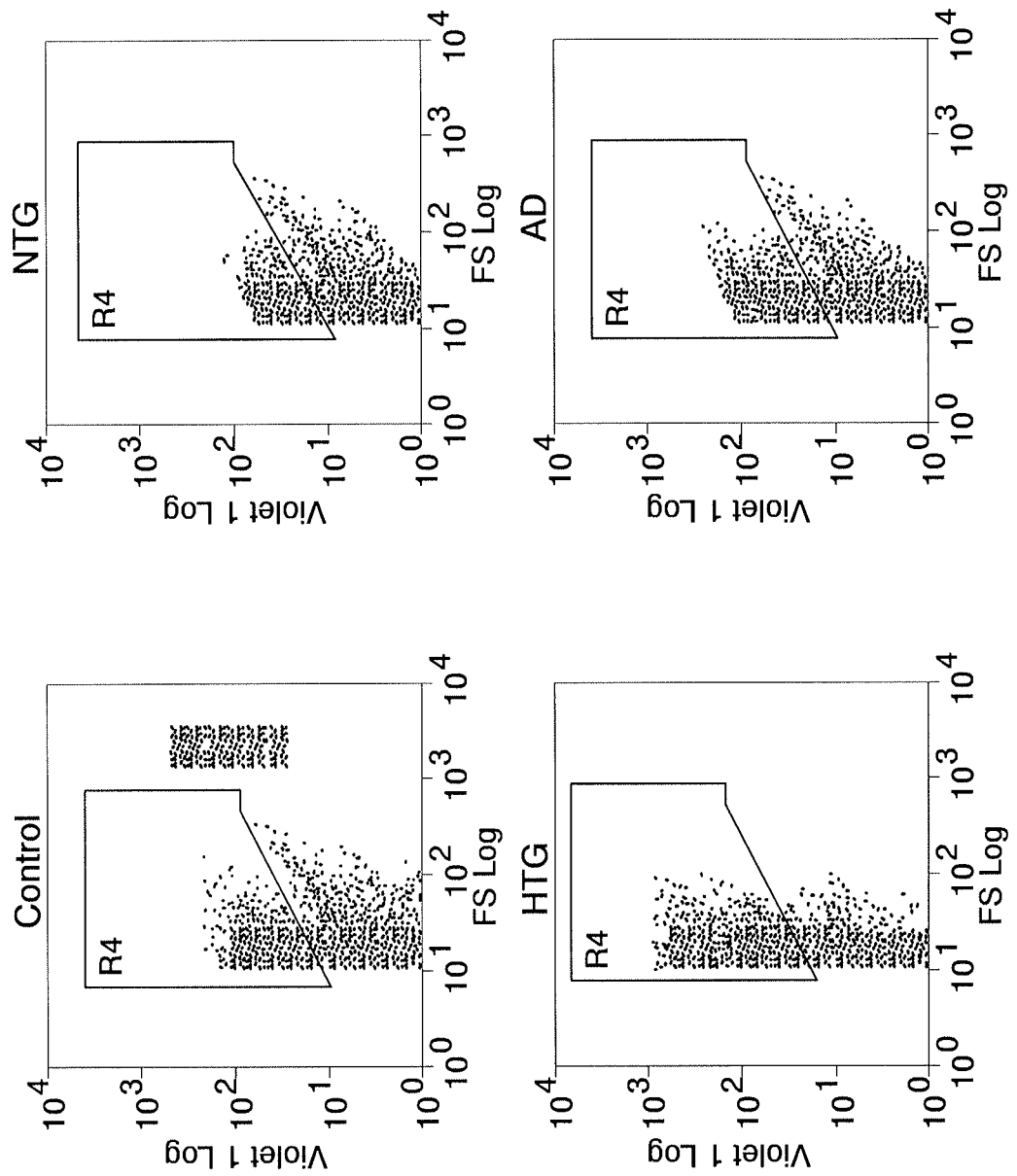
FIG. 6B shows a flow cytometry dot plot of levels of phosphatidylserine-exposing platelets distinguishing SAPs from resting platelets (PAC1-negative and Annexin V positive gated regions R4) for control subjects, NTG patients, POAG patients, and AD patients.

Transglutaminase-active platelet (TAPs) were identified by flow cytometry using a panel of antibodies consisting of anti-PAC-1, Annexin V, and anti-α2-antiplasmin (FIGS. 6A-6C). TAP levels were significantly higher in HTG (P<0.008) and AD (P<0.0001) but not NTG patients compared with healthy controls (FIG. 6D).

Figure 12:
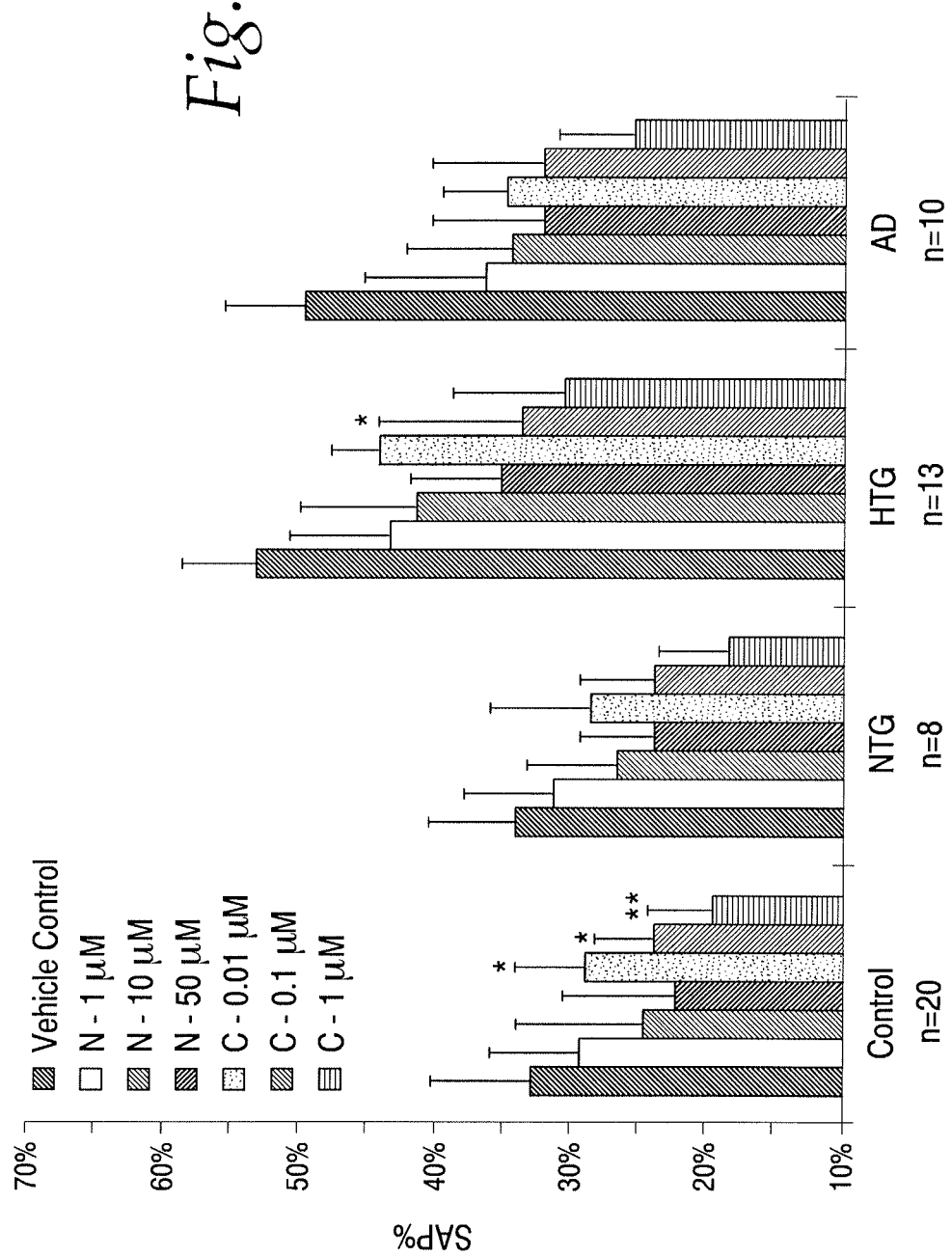
FIG. 12 is a histogram showing the relative amount of SAPs after treatment with low, medium and high doses of naltrexone (N) or curcumin (C) in control subjects, NTG patients, HTG patients and AD patients. * denotes P<0.05, ** denotes P<0.01.

Example 15: Superactivated Platelets after Treatment with Curcumin or Naltrexone Control, NTG, HTG and AD samples were treated with low, medium, or high doses of curcumin or naltrexone in pre-clinical testing. The in vitro doses for naltrexone (N) were 1, 10 and 50 μM and for curcumin (C) were 0.01, 0.1 and 1 μM. The percentage of superactivated platelets observed after treatment is shown in FIG. 12.

Example 16: Superactivated Platelets after Treatment with Resveratrol, Quercetin and Naltrexone Control, NTG, HTG and AD patients were treated with low, medium and high doses of resveratrol (R), quercetin (Q) and naltrexone (N) in combination (RQN), or with low, medium and high doses of resveratrol (R), quercetin (Q) and curcumin (C) in combination (RQC).

Figure 13A:
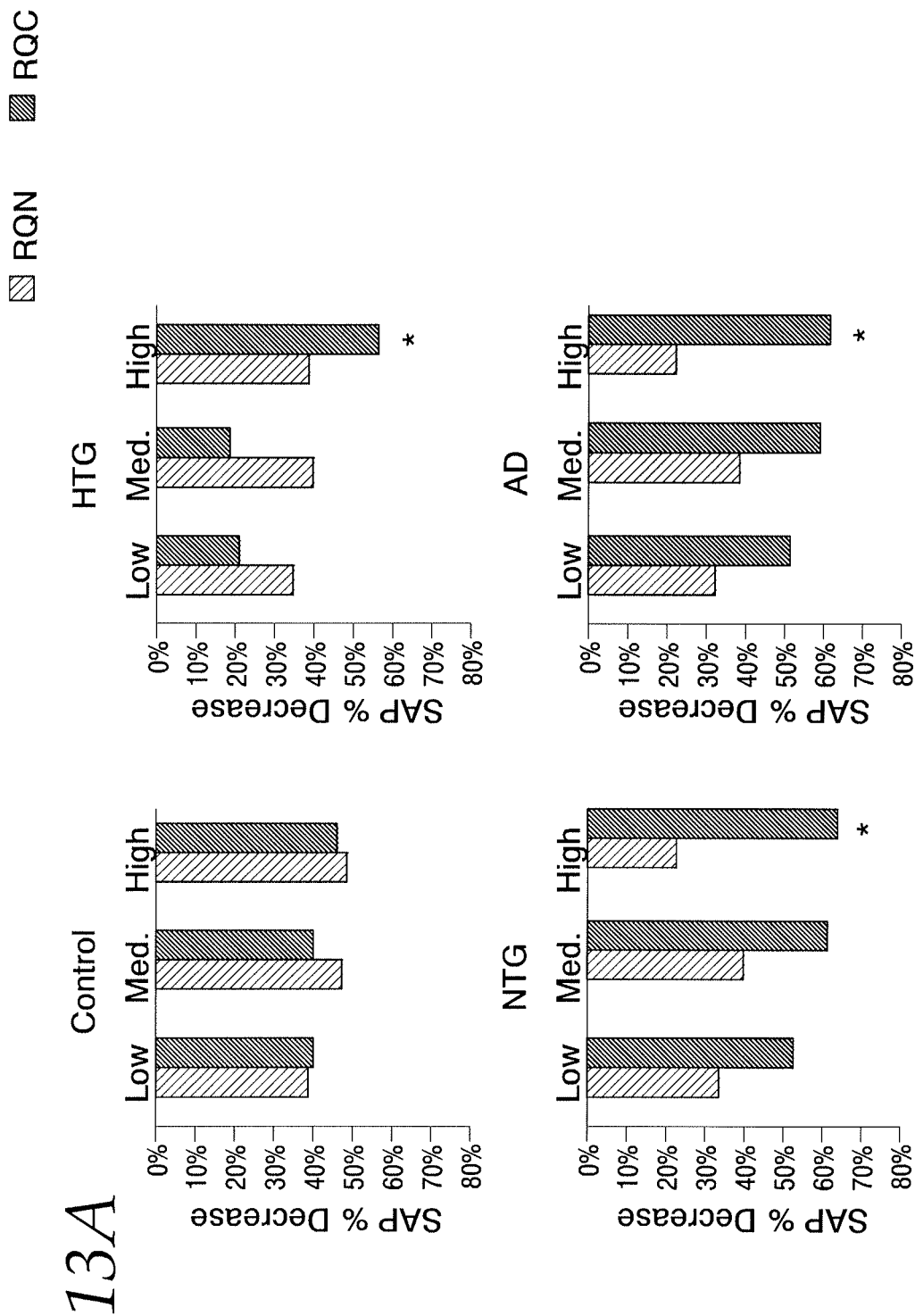
FIG. 13A is a histogram showing the change in SAP levels after treatment with compositions containing resveratrol (5 quercetin (5 and naltrexone (10 μM) (RQN) and with compositions containing resveratrol (5 quercetin (5 μM) and curcumin (0.1 μM) (RQC) in control subjects and HTG, NTG and AD patients. The reported percent decrease in SAP is the difference between control baseline and the decrease in SAP in the treatment group.
Figure 13B:
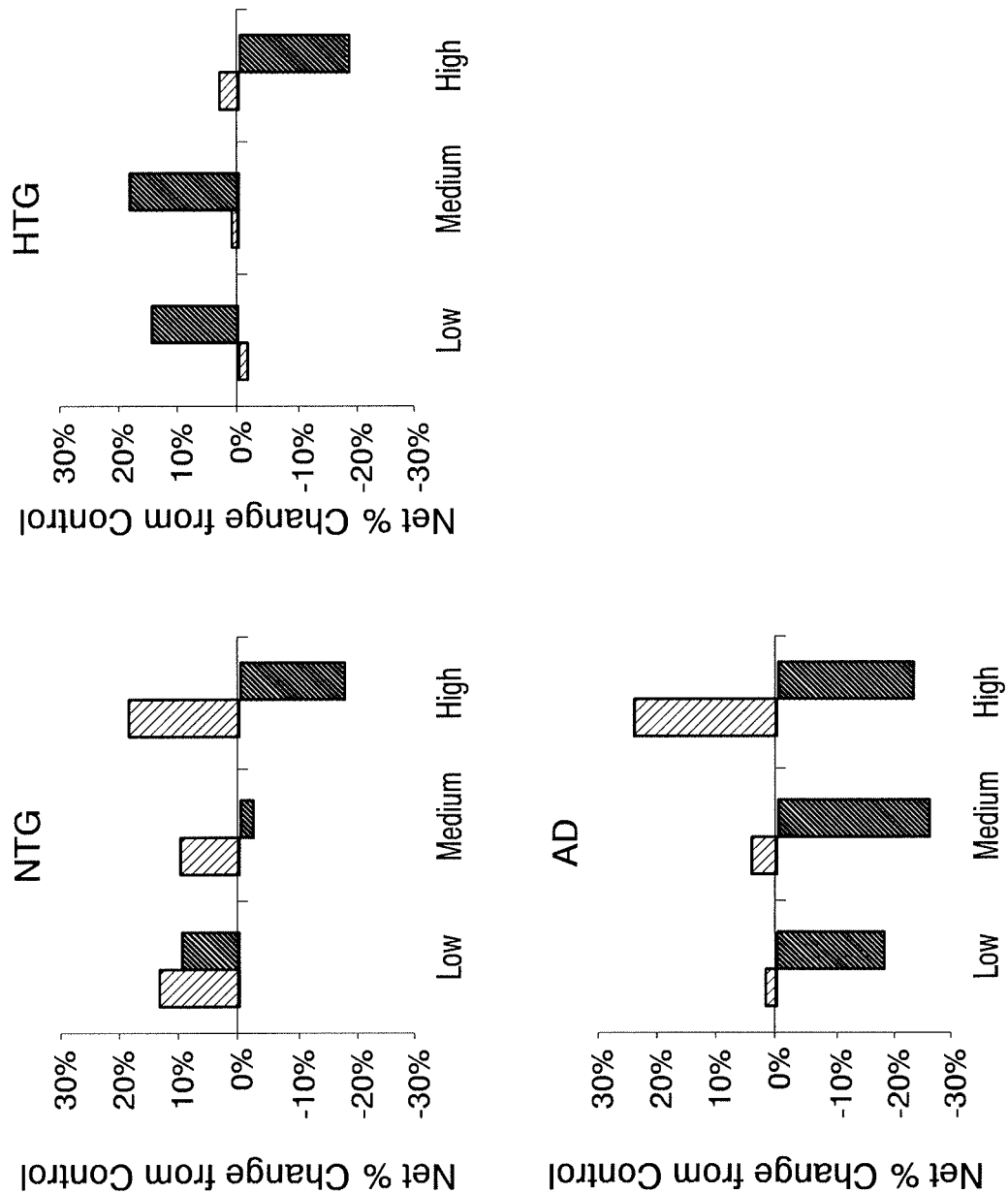
FIG. 13B is a histogram showing the net difference in percent change in SAP levels after treatment with the RQN compositions versus the RQC compositions in FIG. 13A between the control subjects and the NTG, HTG and AD patients.

For RQN, the low dose was 1 μM R, 1 μM Q and 1 μM N; the medium dose was 5 μM R, 5 μM Q and 5 μM N; and the high dose was 10 μM R, 10 μM Q and 10 μM N. For RQC, the low dose was 1 μM R, 1 μM Q and 0.01 μM C; the medium dose was 5 μM R, 5 μM Q and 0.1 μM C; the high dose was 10 μM R, 10 μM Q and 1 μM C. The observed percent decrease in superactivated platelets (SAPs) and percent decrease relative to a control baseline is shown in FIGS. 13A and 13B.

Example 17: Synergy of Active Ingredient Combinations

Figure 14B:
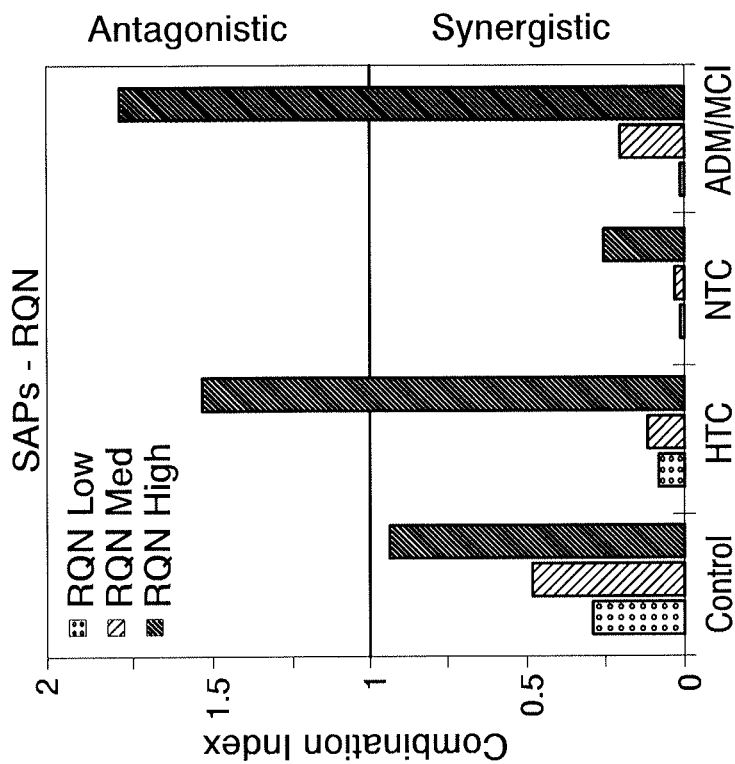
FIG. 14B shows the average Combination Index values for the inhibition of SAPs in control subjects and NTG, HTG and AD/MCI patients at low, medium and high doses of RQN compositions in which the respective mol ratios were: 1:1:1 (low), 5:5:10 (medium), and 10:10:50 (high).
Figure 14A:
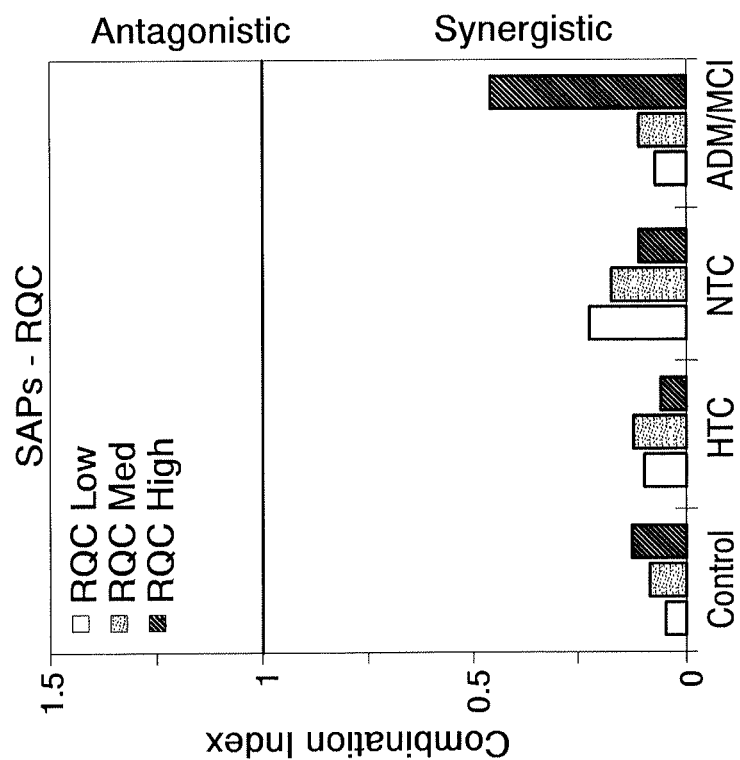
FIG. 14A shows the average Combination Index values for the inhibition of SAPs in control subjects and HTG, and AD/MCI patients at low, medium and high doses of RQC compositions in which the respective mol ratios were: 1:1:0.01 (low), 5:5:0.1 (medium), and 10:10:1 (high).

The average combination index values of (A) low, medium, and high doses of RQC (B) and low, medium, and high doses of RQN for the inhibition of SAPs in control, HTG, NTG, and AD subjects were determined. Molar ratios of RQC were 1:1:0.01 (low), 5:5:0.1 (medium), and 10:10:1 (high). Molar ratios for RQN were 1:1:1 (low), 5:5:10 (medium), and 10:10:50 (high). The Combination Index (CI) theorem derived by Chou-Talalay was calculated for each combination drug treatment of R, Q, and C. The CI is useful in quantifying levels of synergism and antagonism. The theorem is based on the median-effect equation to provide a common link between a single entity and multiple entities. A CI value <1 indicates synergism, a CI equal to 1 indicates additivity, and a CI >1 indicates antagonism (Example 7). RQC was very effective in low, medium and high doses whereas RQN was not as effective. Key: SAPs, superactivated platelets; NTG, normal tension glaucoma; HTG, high tension glaucoma; AD, Alzheimer's disease; RQC, resveratrol+quercetin+curcumin; RQN, resveratrol+quercetin+naltrexone. The results are presented in FIGS. 14A and 14B.

Figure 15:
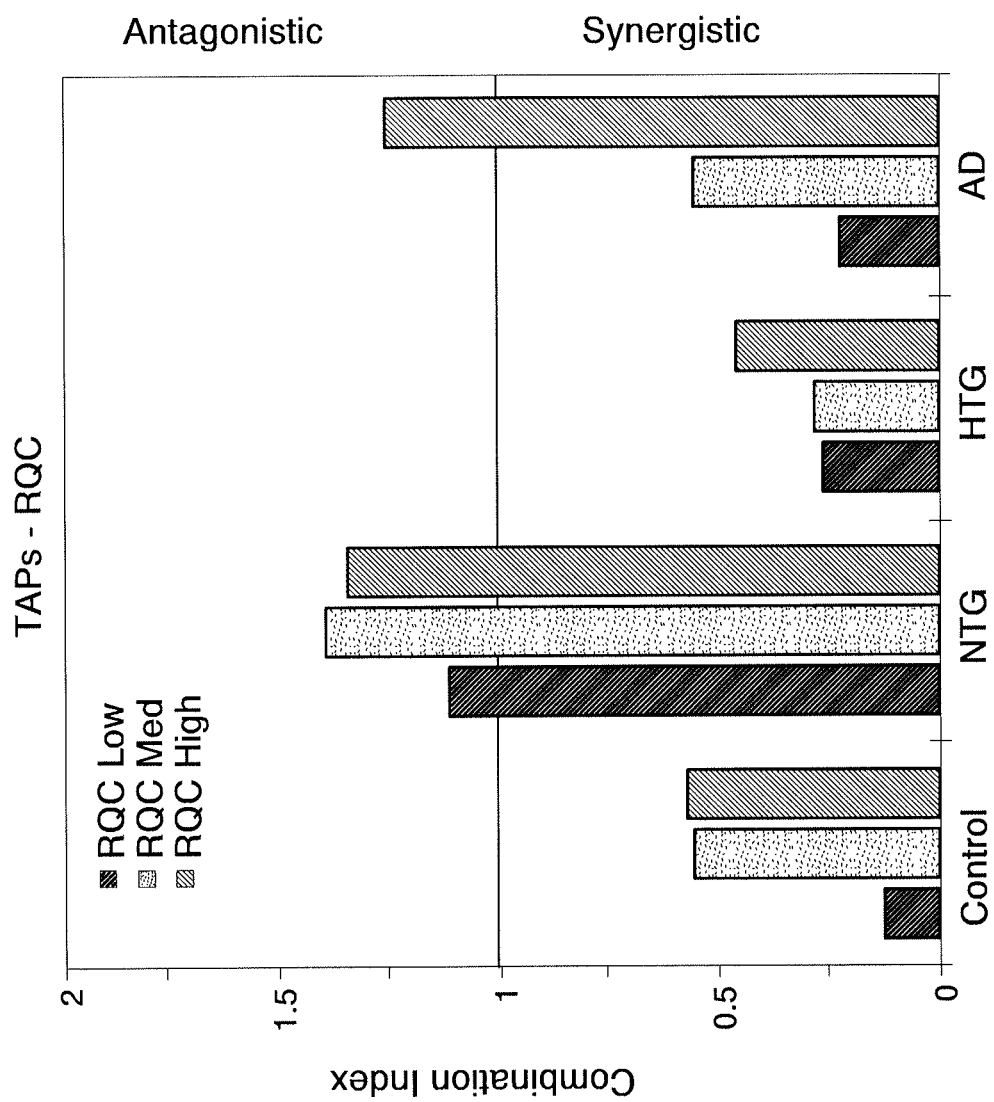
FIG. 15 shows the average Combination Index of low, medium and high doses of RQC compositions for inhibition of TAPs in control subjects, NTG patients, HTG patients, and AD patients. In the ROC compositions the mol ratios were the same as those for FIG. 14A.

Example 18: Average Combination Index for Compositions Containing Resveratrol, Quercetin and Curcumin The average Combination Index of low, medium, and high doses of RQC for the inhibition of transglutaminase-active platelets (TAPs) in control, NTG, HTG, and AD subjects. All combination indexes were based on the mean effect size of each group and were generated using CompuSyn software.[1] Micromolar ratios of RQC were 1:1:0.01 (low), 5:5:0.1 (medium), and 10:10:1 (high). NTG, normal tension glaucoma; HTG, high tension glaucoma; AD, Alzheimer's disease; RQC, resveratrol+quercetin+curcumin; RQN, resveratrol+quercetin+naltrexone. The results are presented in FIG. 15.

[1] Chou T C, Martin N. CompuSyn for drug combinations. A Computer Software for Quantitation of Synergism and Antagonism, and the Determination of IC50, ED50 and LD50 Values. [PC software and user's guide.] (ComboSyn, Paramus, N.J.). 2005.

Example 19: Superactivated Platelet (SAP) and Transglutaminase-Active Platelet (TAP) Levels Over Time Two patients with early-stage Alzheimer's disease were treated with resveratrol (50 mg BID), quercetin (50 mg BID), and curcumin (665 mg BID) in combination. Patient 1 was an 80-year old male with a two-year history of documented Alzheimer's disease. Patient 2 was a 60-year old female with a six-year history of documented Alzheimer's disease.

Figure 16A:
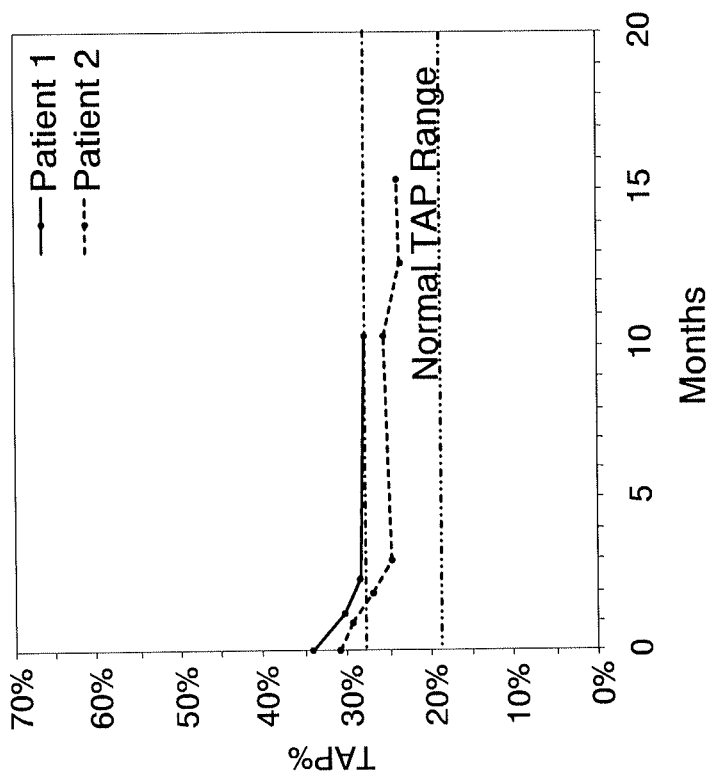
FIG. 16A shows SAP levels over time in two patients suffering from early-stage Alzheimer's disease and receiving orally a dose of a RQC composition (resveratrol, 50 mg BID; quercetin, 50 mg BID; curcumin, 665 mg BID). Patient 1 is an 80-year old male with a two-year history of documented Alzheimer's disease. Patient 2 is a 60-year old female with a six-year history of documented Alzheimer's disease.
Figure 16B:
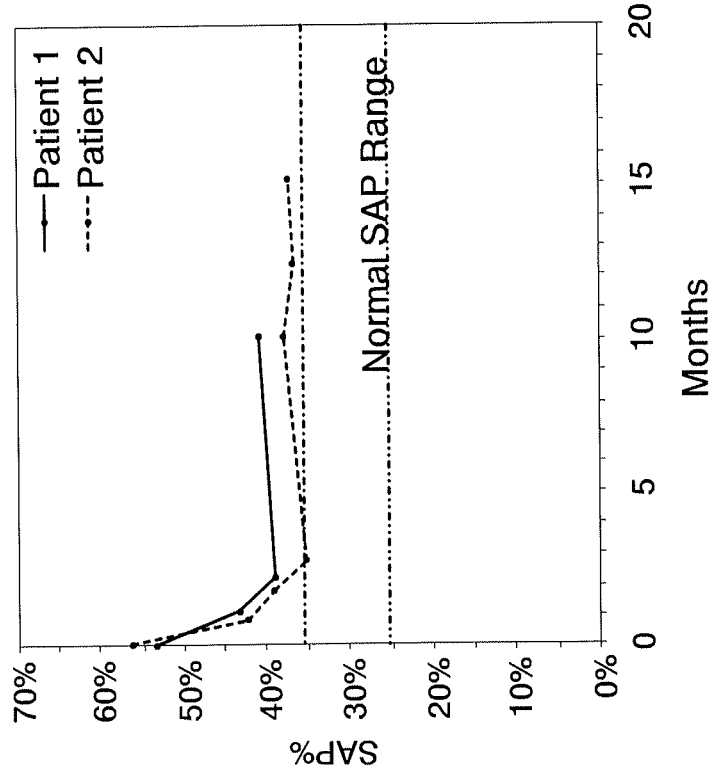
FIG. 16B shows TAP levels over time in the same two patients as described in FIG. 16A, above, receiving orally a dose of a RQC composition (resveratrol, 50 mg BID; quercetin, 50 mg BID; curcumin, 665 mg BID).

SAP and TAP levels of these two patients were determined over a time period of 15 months. The results are shown in Table 14 and FIGS. 16A and 16B. Both patients exhibited a decrease in SAPs and TAPs and nailfold hemorrhages.

TABLE 14

Case Study Results

| Outcome | Baseline | 1 mo. | 2 mo. | 10 mo. | 15 mo. |
|---|---|---|---|---|---|
| Patient 1 - Early-stage Alzheimer's disease | | | | | |
| Nailfold hemorrhages | 2.2 | 2.7 | 2.3 | 0.0 | 0.0 |
| SAP % | 56.28% | 42.37% | 39.23% | 37.68% | 37.36% |
| TAP % | 31.05% | 29.53% | 26.81% | 25.84% | 24.20% |
| MMSE[1] | 27 | 27 | 27 | 27 | 27 |
| PET scan[2] | + | + | + | + | + |
| CSF[3] | − | + | + | + | + |
| Patient 2 - Early-stage Alzheimer's disease | | | | | |
| Nailfold hemorrhages | 12.7 | 18.9 | 8.6 | 3.3 | 2.0 |
| SAP % | 53.68% | 43.66% | 39.07% | 40.65% | 42.37% |
| TAP % | 34.10% | 30.23% | 28.65% | 27.92% | 28.15% |
| MMSE[1] | 24 | 24 | 24 | 24 | 24 |
| PET scan[2] | + | + | + | + | + |
| CSF[3] | — | + | + | + | + |

[1]Mini-Mental State Exam
[2]Positron Emission Tomography scan
[3]Cerebrospinal Fluid

Example 20: Dose-Response Effect of Resveratrol, Quercetin and Curcumin on SAP Levels The dose response effect of resveratrol, quercetin, curcumin, and various combinations thereof on SAP levels in vitro were investigated. Low, medium, and high single doses were for resveratrol (R): Low 1 µM, Medium 5 µM, High 10 µM for quercetin (Q): Low 1 µM, Medium 5 µM, High 10 µM for curcumin (C): Low 0.01 µM, Medium 0.1 µM, High 1 µM The observed results are shown in FIGS. 17A-17L. Effect size is determined by calculating the noted change in SAP percent divided by the baseline SAP percent and is a measure of inhibitory response.

Example 21: Unit Dose Formulations

A uniform powder blend is formulated as a 10-gram batch for encapsulation or packaging in folded paper sachets using the amounts of active pharmaceutical ingredients (APIs) shown in Table 15, below.

TABLE 15

APIs in Exemplary Unit Doses

| | Dose (mg) | Batch (g) |
|---|---|---|
| Formulation w/Naltrexone | | |
| Resveratrol | 2.28 | 1.14 |
| Quercetin | 1.37 | 0.685 |
| Naltrexone | 5.17 | 2.585 |
| Mannitol | 9.98 | 4.99 |
| Sucralose | 0.8 | 0.4 |
| Colloidal silica dioxide | 0.2 | 0.1 |
| Magnesium stearate | 0.2 | 0.1 |
| | 20 | 10 |
| Formulation w/Curcumin | | |
| Resveratrol | 0.97 | 0.49 |
| Quercetin | 1.68 | 0.84 |
| Curcumin | 6.17 | 3.08 |
| Mannitol | 9.98 | 4.99 |
| Sucralose | 0.8 | 0.4 |
| Colloidal silica dioxide | 0.2 | 0.1 |
| Magnesium stearate | 0.2 | 0.1 |
| | 20 | 10 |

One unit dose equivalent of the resulting powder blend is then encapsulated using a tabletop capsule filling machine and hard gelatin or hydroxypropyl-methylcellulose (HPMC) capsules.

The foregoing discussion and the examples are intended as illustrative and are not to be taken as limiting. Still other variants within the spirit and scope of the invention are possible and will readily present themselves to those skilled in the art.

The invention claimed is:

1. A method of inhibiting superactivated platelet aggregation in a subject which comprises administering to the subject an effective amount of a composition containing as active ingredients a synergistic combination of a stilbene, a flavonol and a TLR4/MD2 receptor antagonist,
    wherein the stilbene, the flavonol, and the TLR4/MD2 receptor antagonist plasma concentration is in a respective mol ratio in the range of about 0.1:0.1:1 to about 10:10:50.

2. The method in accordance with claim 1 wherein the stilbene is resveratrol, the flavonol is quercetin, and the TLR4/MD2 receptor antagonist is naltrexone.

3. The method in accordance with claim 1 wherein the stilbene is resveratrol, the flavonol is quercetin, and the TLR4/MD2 receptor antagonist is curcumin.

4. A method of blocking activation of coagulation cascade in a patient which comprises administering to the patient a coagulation cascade blocking amount of a pharmaceutical composition containing as active ingredients a silbene, a flavonol and a TLR4/MD2 receptor antagonist,
   wherein the stilbene, the flavonol, and the TLR4/MD2 receptor antagonist plasma concentration is in a respective mol ratio in the range of about 0.1:0.1:1 to about 10:10:50.

5. A method of treating a patient suffering from a thromboembolic disease which comprises administering to the patient an effective amount of a pharmaceutical composition containing as active ingredients a stilbene, a flavonol and a TLR4/MD2 receptor antagonist,
   wherein the stilbene, the flavonol, and the TLR4/MD2 receptor antagonist plasma concentration is in a respective mol ratio in the range of about 0.1:0.1:1 to about 10:10:50.

6. The method in accordance with claim 4 wherein the stilbene is resveratrol, the flavonol is quercetin, and the TLR4/MD2 receptor antagonist is curcumin.

7. The method in accordance with claim 5 wherein the stilbene is resveratrol, the flavonol is quercetin, and the TLR4/MD2 receptor antagonist is curcumin.

* * * * *